(12) United States Patent
Ashida et al.

(10) Patent No.: US 11,486,877 B2
(45) Date of Patent: Nov. 1, 2022

(54) MEASUREMENT METHOD, MEASURING APPARATUS, PROGRAM, AND METHOD FOR OBTAINING AND DISPLAYING QUALITATIVE DETERMINATION RESULT

(71) Applicant: SYSMEX CORPORATION, Kobe (JP)

(72) Inventors: Mamoru Ashida, Kobe (JP); Motonari Daito, Kobe (JP); Tetsuro Morinaga, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1111 days.

(21) Appl. No.: 15/947,255

(22) Filed: Apr. 6, 2018

(65) Prior Publication Data

US 2018/0292406 A1 Oct. 11, 2018

(30) Foreign Application Priority Data

Apr. 10, 2017 (JP) .............................. JP2017-077862

(51) Int. Cl.
*G01N 33/48* (2006.01)
*G01N 33/50* (2006.01)
(Continued)

(52) U.S. Cl.
CPC ......... *G01N 33/574* (2013.01); *C12Q 1/6851* (2013.01); *G06F 17/15* (2013.01);
(Continued)

(58) Field of Classification Search
CPC ........... G01N 33/574; G01N 33/57415; G01N 33/57446; G16B 40/00; G16B 45/00;
(Continued)

(56) References Cited

U.S. PATENT DOCUMENTS

2002/0142305 A1* 10/2002 Chin .................... C12Q 1/6886
435/6.14
2004/0014067 A1 1/2004 Lyamichev et al.
(Continued)

FOREIGN PATENT DOCUMENTS

CN 104174035 A 12/2014
EP 1867735 A1 12/2007
(Continued)

OTHER PUBLICATIONS

Vogelstein et al. Digital PCR. PNAS, vol. 96, pp. 9236-9241. (Year: 1999).*

(Continued)

*Primary Examiner* — Russell S Negin
(74) *Attorney, Agent, or Firm* — Crowell & Moring LLP

(57) ABSTRACT

Disclosed is a measurement method for measuring a test substance contained in a biological sample based on a predetermined measurement principle, comprising acquiring a first measured value of the test substance using a first measurement reagent, and operating the first measured value to an arithmetic value when measured using a second measurement reagent different from the first measurement reagent, by using arithmetic information designed to make a first cut-off value for the measured value obtained using the first measurement reagent correspond to a second cut-off value for a measured value obtained using the second measurement reagent.

21 Claims, 21 Drawing Sheets

(51) Int. Cl.

| | |
|---|---|
| *G01N 33/574* | (2006.01) |
| *G06F 17/15* | (2006.01) |
| *G06F 17/18* | (2006.01) |
| *G16B 45/00* | (2019.01) |
| *C12Q 1/6851* | (2018.01) |
| *G16B 40/00* | (2019.01) |
| *G16B 25/10* | (2019.01) |

(52) U.S. Cl.
CPC ............. *G06F 17/18* (2013.01); *G16B 40/00* (2019.02); *G16B 45/00* (2019.02); *G01N 33/57415* (2013.01); *G01N 33/57446* (2013.01); *G16B 25/10* (2019.02)

(58) Field of Classification Search
CPC ...... G16B 25/10; G16B 25/00; C12Q 1/6851; C12Q 1/6844; G06F 17/15; G06F 17/18
See application file for complete search history.

(56) References Cited

U.S. PATENT DOCUMENTS

| | | |
|---|---|---|
| 2006/0188911 A1 | 8/2006 | Otomo et al. |
| 2008/0003624 A1 | 1/2008 | Takata et al. |
| 2008/0227094 A1 | 9/2008 | Takata et al. |
| 2011/0021368 A1 | 1/2011 | Tammero et al. |

FOREIGN PATENT DOCUMENTS

| | | |
|---|---|---|
| JP | H9-264893 A | 10/1997 |
| JP | 2008-17832 A | 1/2008 |
| JP | 2015-135282 A | 7/2015 |
| WO | WO 2004/024957 A2 | 3/2004 |
| WO | WO 2014/037811 A2 | 3/2014 |

OTHER PUBLICATIONS

Japanese Office Action dated Apr. 13, 2021 in a counterpart Japanese patent application No. 2017-077862.

Kariyone, K. et al., "Involvement of CRP (C-Reactive Protein) in Serum Albumin Measurement and Its Interference With Nutritional Management Index", *Analytical Bio*—Science, vol. 33, No. 4, 2010, 8 pages (partial English translation).

Rejection Decision dated Apr. 6, 2022 in Chinese patent application No. 201810308127.8.

Guo Zhanjun et al., "Development and Clinical Application of Urine Testing Reagent of Related Factors in Malignant Tumor", Medical Laboratory Science and Clinics, 2006, vol. 17, No. 1, pp. 7-9.

Communication pursuant to Article 94(3) EPC dated Nov. 16, 2021 in European patent application No. 18166290.9.

Chinese Office Action dated Dec. 6, 2021 in Chinese patent application No. 201810308127.8.

* cited by examiner

FIG. 9

| | | | FIRST MEASUREMENT REAGENT 10 | SECOND MEASUREMENT REAGENT 20 |
|---|---|---|---|---|
| CK19 PRIMER REAGENT | PRIMER | CK19 FA primer | 4.0 nmol/mL | 3.2 nmol/mL |
| | | CK19 RA primer | 4.0 nmol/mL | 3.2 nmol/mL |
| | | CK19 F3 primer | 0.25 nmol/mL | 0.2 nmol/mL |
| | | CK19 R3 primer | 0.25 nmol/mL | 0.2 nmol/mL |
| | | CK19 LPF primer | 3.0 nmol/mL | 2.4 nmol/mL |
| | | CK19 LPR primer | 3.0 nmol/mL | 2.4 nmol/mL |
| | dNTPs | 100mM ATP | 1.3 μmol/mL | 0.80 μmol/mL |
| | | 100mM GTP | 1.3 μmol/mL | 0.80 μmol/mL |
| | | 100mM CTP | 1.3 μmol/mL | 0.80 μmol/mL |
| | | 100mM TTP | 1.3 μmol/mL | 0.80 μmol/mL |
| | | 100mM MgSO4 | 9.0 μmol/mL | 7.6 μmol/mL |
| ENZYME REAGENT | | Reverse transcriptase | 1,380 U/mL | 460 U/mL |
| | | DNA polymerase | 16,400 U/mL | 4800 U/mL |

| MEASUREMENT DATE | TIME | SAMPLE ID | CARCINOMA | CK19 DETERMINATION | | MEASURED VALUE [copies/μl] |
|---|---|---|---|---|---|---|
| 16/12/18 | 14:02 | STD-[C1] | | | | |
| 16/12/18 | 14:02 | STD-[C2] | | | | |
| 16/12/18 | 14:04 | STD-[C3] | | | | |
| 16/12/18 | 14:06 | QC-[CK19-PC] | | | | |
| 16/12/18 | 14:06 | QC-[NC] | | | | |
| 16/12/18 | 14:41 | A2 | BC | (Neg.) | (−) | <1.6E+02 |
| 16/12/18 | 14:41 | A15 | BC | (Neg.) | (−) | <1.6E+02 |
| 16/12/18 | 14:43 | A104 | BC | (Pos.) | (+) | 4.3E+03 |
| 16/12/18 | 14:43 | A52 | BC | (Pos.) | (++) | 1.2E+05 |
| 16/12/18 | 14:45 | A8 | BC | (Neg.) | (−) | <1.6E+02 |

MEASUREMENT METHOD, MEASURING APPARATUS, PROGRAM, AND METHOD FOR OBTAINING AND DISPLAYING QUALITATIVE DETERMINATION RESULT

CROSS REFERENCE TO RELATED APPLICATIONS

This application claims priority from prior Japanese Patent Application No. 2017-077862, filed on Apr. 10, 2017, entitled "MEASUREMENT METHOD, MEASURING APPARATUS, PROGRAM, METHOD FOR OBTAINING ARITHMETIC EXPRESSION AND METHOD FOR DISPLAYING QUALITATIVE DETERMINATION RESULT", the entire contents of which are incorporated herein by reference.

TECHNICAL FIELD

As measurement conditions for measuring examination items in clinical examination, various types are proposed, as a result of considering improvements for improving measurement accuracy and improving measurement efficiency. The measurement conditions may include conditions such as the measurement reagent to be used, the measurement temperature, the amount and concentration of the specimen used for measurement, and the amount and concentration of the measurement reagent. When a plurality of types of measurement conditions is used for the same examination item, each measured value obtained under each measurement condition does not necessarily completely match. Thus, it may be necessary to grasp the mutual correspondence relation of each measured value obtained under each measurement condition. In order to grasp the mutual correspondence relation of each measured value obtained under each measurement condition, there is a case where the measured value obtained under a certain measurement condition is operated to the value when measured under other measurement condition.

Conventionally, it is known that the correspondence relation between measured values is grasped, from a plurality of measured values obtained by measuring the same plural specimens, using different measurement reagents used for the same examination item (for example, Kazuko Kariyone et al., "Involvement of C-reactive protein in serum albumin measurement and its interference with nutritional management index", Analytical Bio-Science, 2010, Vol. 33, No. 4, p. 383-390).

BACKGROUND

Kazuko Kariyone et al., "Involvement of C-reactive protein in serum albumin measurement and its interference with nutritional management index", Analytical Bio-Science, 2010, Vol. 33, No. 4, p. 383-390, discloses that, as shown in FIG. 28, in a coordinate plane in which the first measured value by a first measurement method using a first measurement reagent is taken on the vertical axis and the second measured value by a second measurement method using a second measurement reagent is taken on the horizontal axis, a correlation diagram 900 plotting measurement results 901 obtained by measuring the same specimen is created, and a regression line 902 is obtained from the correlation diagram 900.

When clinical judgment is made based on the measured values obtained in clinical examination, different clinical judgments are made with a predetermined cut-off value as a boundary. When a regression line is obtained as in, Kazuko Kariyone et al., "Involvement of C-reactive protein in serum albumin measurement and its interference with nutritional management index", Analytical Bio-Science, 2010, Vol. 33, No. 4, p. 383-390, the first measured value can be operated to the corresponding value of the second measured value. However, the regression line is approximate only and there is a residual, thus the clinical judgment before and after operation of the first measured value may not match by the operation, in the vicinity of the cut-off value. Therefore, it is desirable to suppress change in clinical judgment before and after operation, when operating the measured value obtained under a certain measurement condition to the value in the case of using another measurement condition in clinical examination.

SUMMARY OF THE INVENTION

The scope of the present invention is defined solely by the appended claims, and is not affected to any degree by the statements within this summary.

A measurement method according to a first aspect of this invention is a measurement method for measuring a test substance (90) contained in a biological sample based on a predetermined measurement principle, including acquiring a first measured value (11) of the test substance (90) using a first measurement reagent (10), and operating the first measured value (11) to an arithmetic value (22) when measured using a second measurement reagent (20) different from the first measurement reagent (10), by using arithmetic information (30) designed to make a first cut-off value (15) for the measured value obtained using the first measurement reagent (10) correspond to a second cut-off value (25) for a measured value obtained using the second measurement reagent (20). Here, operation is a broad concept that refers to calculation processing such as arithmetic operations, comparative operations for comparing sizes of numeric values, and logical operations. The arithmetic value (22) is a broad concept including not only the case of being calculated by an arithmetic expression but also the case of being operated using a correspondence table between the first measured value (11) and the second measured value (21) when measured using the second measurement reagent (20).

A measuring apparatus according to a second aspect of this invention is a measuring apparatus (100) for measuring a test substance (90) contained in a biological sample based on a predetermined measurement principle, including a measurement unit (110) for acquiring a first measured value (11) corresponding to the test substance (90) using a first measurement reagent (10), and an operational unit (120) for operating the first measured value (11) to an arithmetic value (22) when measured using a second measurement reagent (20) different from the first measurement reagent (10), by using arithmetic information (30) designed to make a first cut-off value (15) for the measured value obtained using the first measurement reagent (10) correspond to a second cut-off value (25) for a measured value obtained using the second measurement reagent (20).

A measuring apparatus according to a third aspect of this invention includes a measurement unit (410) for acquiring a measured value (51) of a test substance (90) under a first measurement condition, a determination unit (420) for performing qualitative determination on a specimen containing the test substance (90) by comparing the measured value (51) with a cut-off value (55), an operational unit (430) for obtaining an arithmetic value (61) operated so as to correspond to a measured value when the measured value (51) is measured under a second measurement condition, and a display unit (440) for displaying the arithmetic value (61) and a qualitative determination result (62).

A program according to a fourth aspect of this invention is a program (250) for measuring a test substance (90) contained in a biological sample based on a predetermined measurement principle, which makes a computer acquire a first measured value (11) of the test substance (90) measured using a first measurement reagent (10), makes a computer acquire arithmetic information (30) designed to make a first cut-off value (15) for the measured value obtained using the first measurement reagent (10) correspond to a second cut-off value (25) for a measured value obtained using a second measurement reagent (20) different from the first measurement reagent (10), and makes a computer operate the first measured value (11) to an arithmetic value (22) when measured using the second measurement reagent (20), using the arithmetic information (30).

A method for obtaining an arithmetic expression according to a fifth aspect of this invention is a method of acquiring an arithmetic expression (31) for operating a measured value obtained by measuring a test substance (90) contained in a biological sample based on a predetermined measurement principle, including acquiring a first cut-off value (15) for a first measured value (11) of the test substance (90) obtained using a first measurement reagent (10), acquiring a second cut-off value (25) for a second measured value (21) of the test substance (90) obtained using a second measurement reagent (20), and acquiring a function for matching an arithmetic value (22) of the first cut-off value (15) with the second cut-off value (25), based on the first cut-off value (15) and the second cut-off value (25), as the arithmetic expression (31) of the measured value obtained using the first measurement reagent (10) and the measured value obtained using the second measurement reagent (20).

A method for displaying a qualitative determination result according to a sixth aspect of this invention acquires a measured value (51) of a test substance (90) under a first measurement condition, performs qualitative determination on a specimen containing the test substance (90) by comparing the measured value (51) with a cut-off value (55), obtains an arithmetic value (61) operated so as to correspond to a measured value when the measured value (51) is measured under a second measurement condition, and displays the arithmetic value (61) and a qualitative determination result (62).

A program according to a seventh aspect of this invention is a program for displaying a qualitative determination result based on a measurement result of a test substance (90), which makes a computer acquire a measured value (51) of the test substance (90) measured under a first measurement condition, and makes the computer perform qualitative determination on a specimen containing the test substance (90) by comparing the measured value (51) with a cut-off value (55), makes the computer obtain an arithmetic value (61) operated so as to correspond to a measured value when the measured value (51) is measured under a second measurement condition, and makes the computer display the arithmetic value (61) and a qualitative determination result (62).

BRIEF DESCRIPTION OF THE DRAWINGS

FIG. 9 is a diagram showing composition examples of a first measurement reagent and a second measurement reagent;

FIG. 11 is a diagram showing a first example of a measurement result display screen;

FIG. 12 is a diagram showing a second example of a measurement result display screen;

DETAILED DESCRIPTION OF THE PREFERRED EMBODIMENTS

Hereinafter, embodiments will be described with reference to the drawings.

[Outline of Measurement Method]

Figure 1:
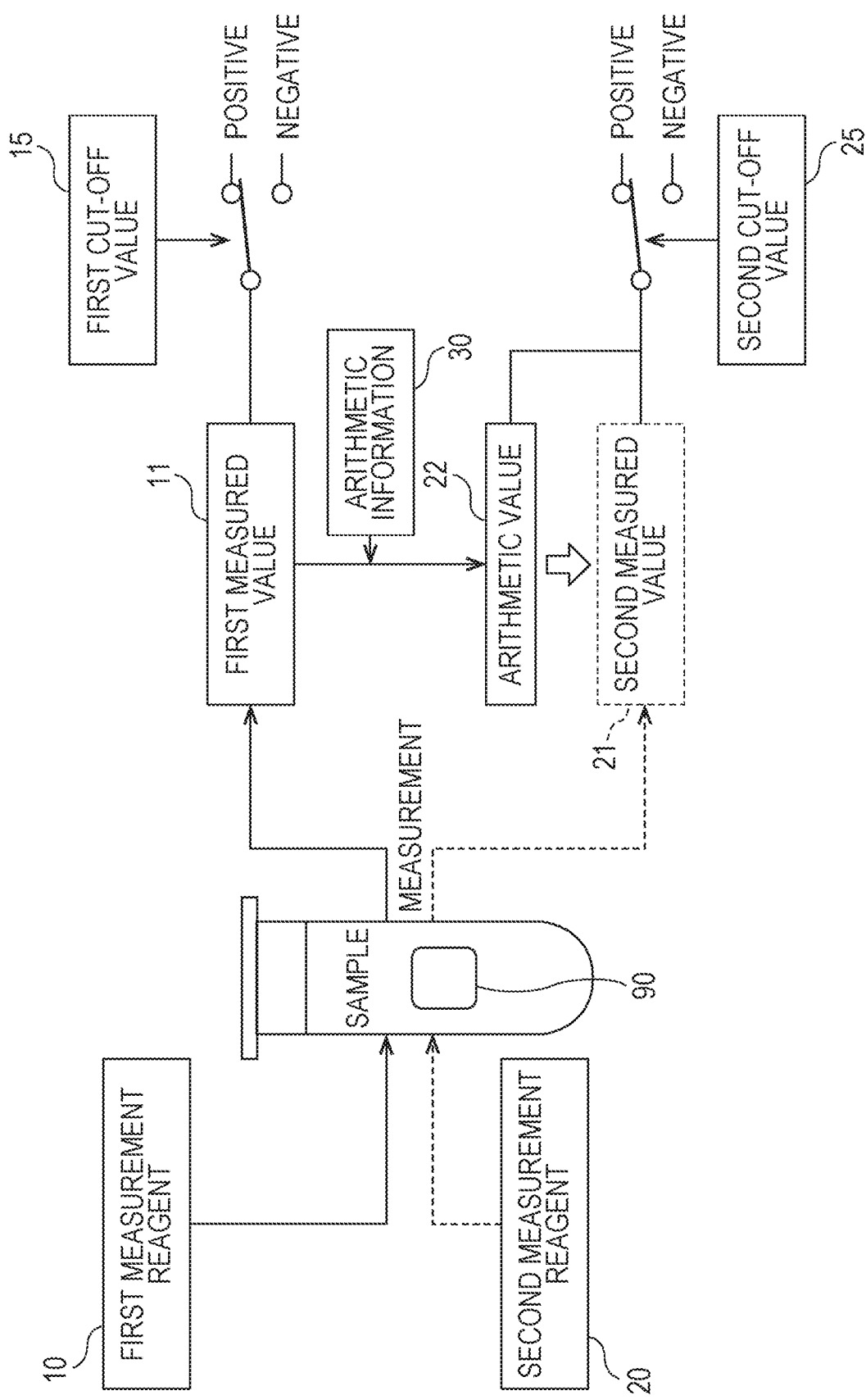
FIG. 1 is a diagram for describing an outline of a measurement method.

With reference to FIG. 1, the outline of the measurement method according to this embodiment will be described.

The measurement method of this embodiment is a measurement method for measuring a test substance 90 contained in a biological sample based on a predetermined measurement principle. The biological sample includes a sample acquired from an organism, an isolate or extract from the biological sample, or a sample pretreated on the biological sample. The biological sample includes, for example, tissue pieces, cells, body fluids such as blood and tissue fluid and the like obtained from a living body.

The test substance 90 is a substance to be measured and is a substance contained in the biological sample. The test substance 90 is, for example, a nucleic acid such as DNA (deoxyribonucleic acid) or RNA (ribonucleic acid), a cell and intracellular substance, an antigen or antibody, a protein, a peptide, or the like. In this embodiment, the test substance 90 is a marker substance that provides a measured value to be evaluated in clinical judgment in clinical examination.

The measurement method of this embodiment includes acquiring a first measured value 11 of a test substance 90 using a first measurement reagent 10 and operating the first measured value 11 to an arithmetic value 22 when measured using a second measurement reagent 20, using arithmetic information 30. That is, the first measured value 11 obtained under the measurement condition using the first measurement reagent 10 is converted into the arithmetic value 22 corresponding to a measured value obtained when measured under the measurement condition using the second measurement reagent 20.

Both the first measurement reagent 10 and the second measurement reagent 20 are reagents used for measuring the test substance 90 contained in a biological sample based on a predetermined measurement principle. The measurement principle specifies the law that enables the measurement, the reaction mechanism accompanied by the measurement, and the action mechanism of chemical substances. The reagent contains a chemical substance used for detection or quantification of the test substance 90 by a chemical method. Based on the same measurement principle, the first measurement reagent 10 and the second measurement reagent 20 generate chemical reactions with the test substance 90 or a substance associated with the test substance 90, so that the test substance 90 can be directly, or indirectly via other associated substances. By the measurement based on the predetermined measurement principle, the measured value relating to the test substance 90 is acquired.

The first measurement reagent 10 and the second measurement reagent 20 are reagents different from each other. For example, in the case where the concentrations of components contained in the first measurement reagent 10 and the second measurement reagent 20 are different, when measurement is each performed on the same biological sample based on the same measurement principle, the obtained measured values reflect the same test substance 90, but they are values different from each other. Therefore, for the first measurement reagent 10 and the second measurement reagent 20, cut-off values for clinical judgment are respectively set for the measured values obtained by measurement. Clinical judgment is, for example, positive when the measured value is not less than the cut-off value, negative when it is less than the cut-off value, or the like.

As described above, the first measurement reagent 10 and the second measurement reagent 20 are reagents used for measuring the same test substance 90 based on the same measurement principle, and it is desirable that clinical judgments based on the obtained measured values become also identical to each other. Typical examples of the first measurement reagent 10 and the second measurement reagent 20 are a case where the second measurement reagent 20 is a conventional reagent commonly used for a specific examination item for measuring the test substance 90, and the first measurement reagent 10 is an improved reagent newly developed for the same examination item. Improved reagents improve convenience by, for example, improving reaction efficiency and accuracy and relaxing conditions of use during measurement.

As an example, when the reaction efficiency is different between the first measurement reagent 10 and the second measurement reagent 20, the quantitative values measured under the same condition are different, thus the cut-off values that provide the same clinical judgment are different from each other. That is, for the first measured value 11 obtained using the first measurement reagent 10, clinical judgment is made based on the first cut-off value 15, and for the second measured value 21 obtained using the second measurement reagent 20, clinical judgment is made based on the second cut-off value 25. However, when clinical data measured using the second measurement reagent 20 is accumulated in a clinical site, it becomes difficult to compare the first measured value 11 obtained by a newly introduced first measurement reagent 10 and the clinical data, thus, for comparison, it may be necessary to grasp the correspondence relation between the first measured value 11 and the second measured value 21.

Therefore, in this embodiment, the first measured value 11 is operated to the arithmetic value 22 when measured using the second measurement reagent 20, using the arithmetic information 30. Therefore, the arithmetic value 22 is a measured value corresponding to the second measured value 21 obtained when measured using the second measurement reagent 20 for the same sample from which a certain first measured value 11 was obtained. The arithmetic value 22 makes it possible to perform the same clinical judgment by the second cut-off value 25 for the second measured value 21.

The arithmetic information 30 is information for operating the first measured value 11 obtained using the first measurement reagent 10 to the arithmetic value 22 corresponding to the second measured value 21 obtained using the second measurement reagent 20. The arithmetic information 30 may be, for example, an arithmetic expression including a function of the first measured value 11 and the arithmetic value 22, or may be an arithmetic table that makes the first measured value 11 correspond to the arithmetic value 22. In the case of the arithmetic table, the arithmetic information 30 includes a plurality of numerical sets of the first measured value 11 and the arithmetic value 22 corresponding thereto at predetermined numerical intervals. An intermediate first measured value 11 that is not defined in the arithmetic table can be obtained by interpolation. In the case of an arithmetic expression, the arithmetic value 22 is obtained by substituting the first measured value 11 obtained using the first measurement reagent 10 into the arithmetic expression and performing operation.

The arithmetic information 30 is designed to make the first cut-off value 15 for the measured value obtained using the first measurement reagent 10 correspond to the second cut-off value 25 for a measured value obtained using the second measurement reagent 20 different from the first measurement reagent 10. That is, according to the arithmetic information 30, the first cut-off value 15 and the second cut-off value 25 correspond substantially one to one each other. Therefore, when performing operation based on the arithmetic information 30, a first measured value 11 having the first cut-off value 15 or more is operated as an arithmetic value 22 having the second cut-off value 25 or more, and a first measured value 11 having less than the first cut-off value 15 is operated as an arithmetic value 22 having less than the second cut-off value 25. However, as the arithmetic information 30, the arithmetic value 22 of the first cut-off value 15 is not completely matched with the second cut-off value 25, but the first cut-off value 15 and the second cut-off value 25 may be made correspond to each other, for example, to a degree of matching within a range smaller than the error range of the measured value.

As described above, in the measurement method of this embodiment, the first measured value 11 obtained using the first measurement reagent 10 can be operated to the arithmetic value 22 when measured using the second measurement reagent 20, under the condition that the first cut-off value 15 and the second cut-off value 25 are associated with each other, using the arithmetic information 30. In other words, in the case of operating using a regression equation obtained from the measurement result obtained by measuring the same specimen using each of the first measurement reagent 10 and the second measurement reagent 20, the arithmetic value is determined irrespective of the cut-off value. However, according to the arithmetic information 30 in which the cut-off values are made to correspond to each other, the arithmetic value 22 can be determined so that the relationship between the first measured value 11 and the first cut-off value 15 is maintained in the relationship between the arithmetic value 22 and the second cut-off value 25 as it is. As a result, it is possible to suppress change in clinical judgment before and after operation, when operating the measured value obtained under the measurement condition using the first measurement reagent 10 to the value when measured under the measurement condition using the second measurement reagent 20 in clinical examination.

In the example of FIG. 1, the first cut-off value 15 and the second cut-off value 25 are thresholds for performing qualitative determination on at least one of a biological sample and a specimen containing the biological sample. This makes it possible to operate the measured value, without changing the qualitative determination such as positive or negative for the examination item in clinical examination. As a result, in association with qualitative determination, the arithmetic value 22 of the first measured value 11 measured using the first measurement reagent 10 this time can be compared with the data measured using the second measurement reagent 20 in the past, and the arithmetic value 22 can be used for diagnosis and statistically handled along with the data measured using the second measurement reagent 20.

In the example of FIG. 1, qualitative determination indicates the presence or absence of suspected disease or the degree of suspicion of disease. This makes it possible to determine the presence or absence of suspected disease and the degree of disease without changing the qualitative determination, whichever of the first measured value 11 before operation and the arithmetic value 22 after operation is used.

In the example of FIG. 1, qualitative determination is performed on at least one of the biological sample in which the test substance 90 has been measured and a specimen containing the biological sample, based on the first cut-off value 15 and the first measured value 11, or the second cut-off value 25 and the arithmetic value 22. This makes it possible to perform qualitative determination using not only the operation of the first measured value 11 but also the first measured value 11 or the arithmetic value 22, so that the qualitative determination result can be used for clinical examination.

[Measuring Apparatus]

Next, an example of a measuring apparatus that implements the measurement method according to this embodiment will be described.

Figure 2:
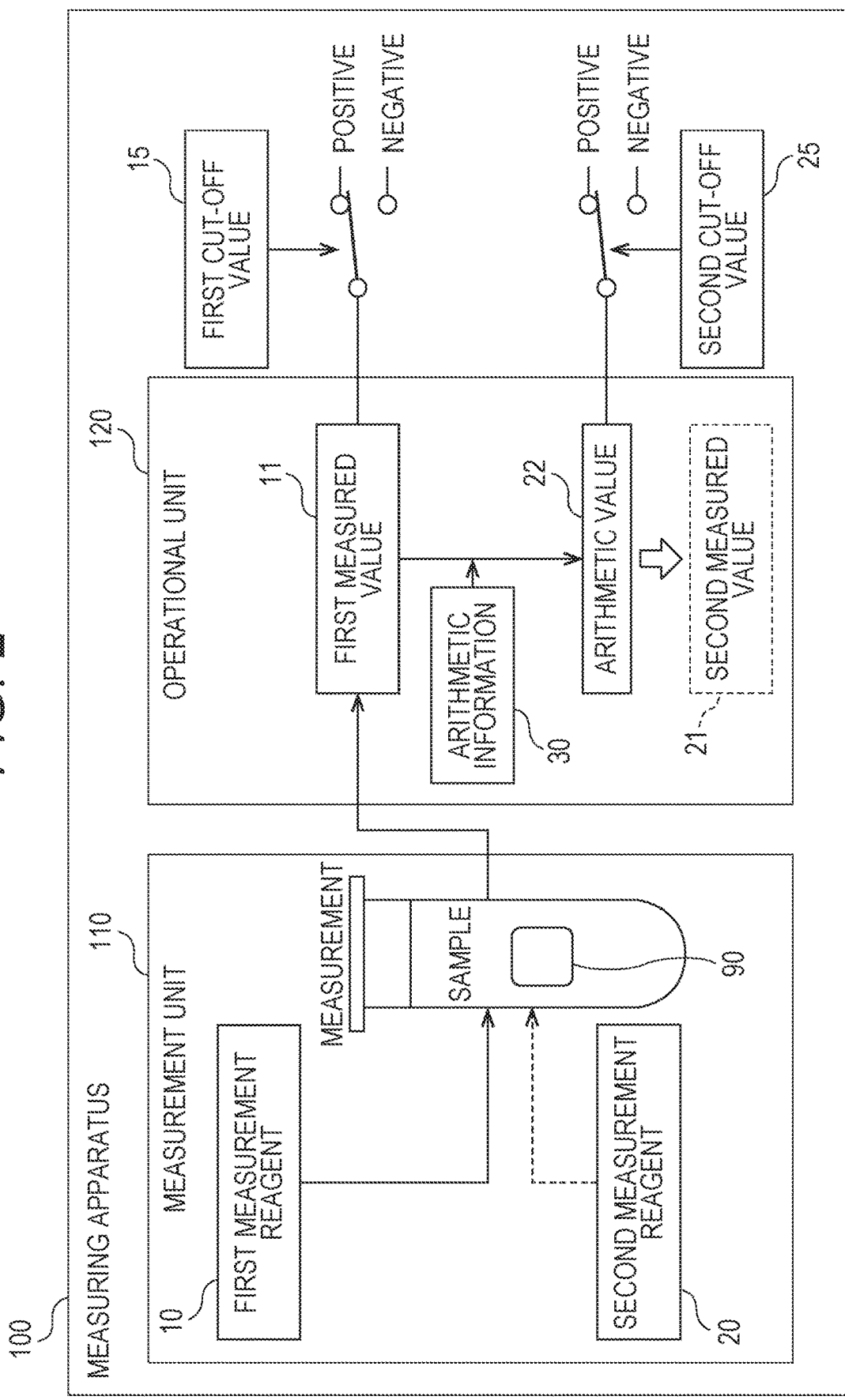
FIG. 2 is a diagram for describing an outline of a measuring apparatus.

As shown in FIG. 2, a measuring apparatus 100 is a measuring apparatus that measures a test substance 90 contained in a biological sample based on a predetermined measurement principle. The measuring apparatus 100 includes a measurement unit 110 for acquiring a first measured value 11 corresponding to the test substance 90 using a first measurement reagent 10, and an operational unit 120 for operating the first measured value 11 to an arithmetic value 22 when measured using a second measurement reagent 20, using arithmetic information 30.

The measurement unit 110 has a function of reacting the first measurement reagent 10 with, for example, a test substance 90 or a substance associated with the test substance 90. The measurement unit 110 has a function of directly or indirectly measuring the test substance 90, accompanying the test substance 90 or the substance associated with the test substance 90 and the chemical reaction. By measurement based on a predetermined measurement principle, the measurement unit 110 acquires a measured value relating to the test substance 90.

The operational unit 120 acquires the first measured value 11 obtained using the first measurement reagent 10 by the measurement unit 110. The operational unit 120 obtains the arithmetic value 22 using the arithmetic information 30 described above. As described above, the arithmetic information 30 is designed to make a first cut-off value 15 for the measured value obtained using the first measurement reagent 10 correspond to a second cut-off value 25 for a measured value obtained using the second measurement reagent 20 different from the first measurement reagent 10. The arithmetic information 30 may be in the form of an arithmetic table or an arithmetic expression. When the arithmetic information 30 is an arithmetic table, the operational unit 120 operates the first measured value 11 to the corresponding arithmetic value 22, by referring to the arithmetic table or by an interpolation using values defined in the arithmetic table. When the arithmetic information 30 is an arithmetic expression, the operational unit 120 substitutes the first measured value 11 into the arithmetic expression, and operates the first measured value 11 to the corresponding arithmetic value 22.

In the measuring apparatus 100 of this embodiment, according to the above configuration, the first measured value 11 obtained using the first measurement reagent 10 can be operated to an arithmetic value 22 when measured using a second measurement reagent 20, under the condition that the first cut-off value 15 and the second cut-off value 25 are associated with each other, using the arithmetic information 30. In other words, in the case of operating using a regression equation obtained from the measurement result obtained by measuring the same specimen using each of the first measurement reagent 10 and the second measurement reagent 20, the arithmetic value is determined irrespective of the cut-off value. However, according to the arithmetic information 30 in which the cut-off values are made to correspond to each other, the arithmetic value 22 can be determined so that the relationship between the first measured value 11 and the first cut-off value 15 is maintained in the relationship between the arithmetic value 22 and the second cut-off value 25 as it is. As a result, it is possible to suppress change in clinical judgment before and after operation, when operating the measured value obtained under the measurement condition using the first measurement reagent 10 to the value when measured under the measurement condition using the second measurement reagent 20 in clinical examination.

The measuring apparatus 100 is configured to perform qualitative determination on at least one of the biological sample in which the test substance 90 has been measured and a specimen containing the biological sample, based on the first cut-off value 15 and the first measured value 11, or the second cut-off value 25 and the arithmetic value 22. This makes it possible to perform qualitative determination using not only the operation of the first measured value 11 but also the first measured value 11 or the arithmetic value 22, so that the qualitative determination result can be used for clinical examination.

[Arithmetic Information]

Figure 3:
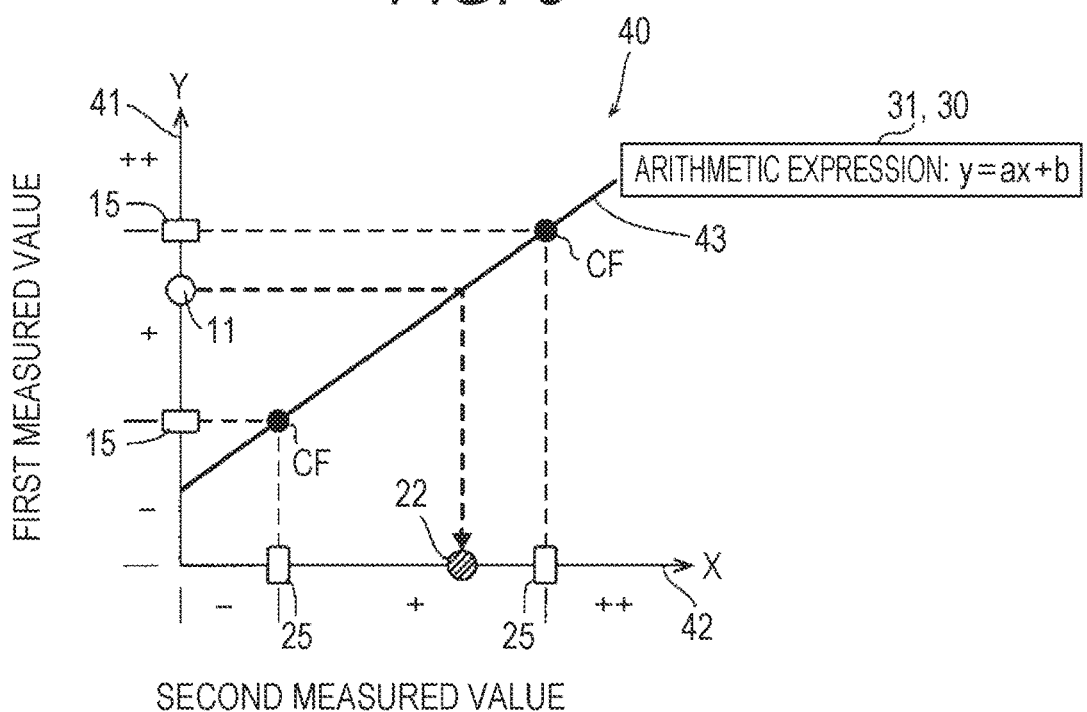
FIG. 3 is a diagram showing an example of an arithmetic expression in the case of two cut-offs.

FIG. 3 shows an example of arithmetic information 30. FIG. 3 is a correlation diagram in which a first coordinate axis 41 representing a first measured value 11 obtained using a first measurement reagent 10 and a second coordinate axis 42 representing a second measured value 21 obtained using a second measurement reagent 20 are set, and the relationship between the first measured value 11 and the second measured value 21 is shown on a coordinate plane 40 between the first coordinate axis 41 and the second coordinate axis 42. In FIG. 3, the first coordinate axis 41 is taken on the Y axis, and the second coordinate axis 42 is taken on the X axis.

In FIG. 3, the arithmetic information 30 includes an arithmetic expression 31 of the measured value obtained using the first measurement reagent 10 and the measured value obtained using the second measurement reagent 20. In FIG. 3, the arithmetic value 22 on the X axis is obtained as an X coordinate, from the intersection of a Y coordinate corresponding to the first measured value 11 obtained by measurement and an operation line 43 defined by the arithmetic expression 31.

In FIG. 3, the arithmetic expression 31 is a function set so as to operate the first measured value 11 that matches the first cut-off value 15 to the arithmetic value 22 that matches the second cut-off value 25. That is, the operation line 43 defined by the arithmetic expression 31 is set so as to pass through a point CF having the first cut-off value 15 as the Y coordinate and the second cut-off value 25 as the X coordinate.

Thereby, the first cut-off value 15 and the second cut-off value 25 before and after operation match with each other, so that the clinical judgment based on the first measured value 11 and the first cut-off value 15 and the clinical judgment based on the arithmetic value 22 and the second cut-off value 25 can be matched with each other. As a result, it is possible to reliably prevent change in clinical judgment before and after operation of the first measured value 11.

In FIG. 3, the arithmetic expression 31 is a linear function expressed by y=ax+b, and it may be a quadratic function or a tertiary or higher function.

The number of cut-off values may be one or more. FIG. 3 shows an example of two pairs of the first cut-off value 15 and the second cut-off value 25 corresponding to the first cut-off value 15. In FIG. 3, the qualitative determination is performed in three stages of (−, +, ++). The first pair is a cut-off value of (−/+), and the second pair is a cut-off value of (+/++).

In this embodiment, when there are a plurality of pairs of the first cut-off value 15 and the second cut-off value 25 corresponding to the first cut-off value 15, the arithmetic information 30 includes a plurality of the arithmetic expressions 31 set for each section between adjacent cut-off values.

This makes it possible to set the arithmetic expression 31 for each section between adjacent cut-off values. Thus, even when there is a plurality of cut-off values, it is possible to reliably prevent change in clinical judgment determined using each cut-off value as a boundary before and after operation. Even when there is a plurality of sections, the arithmetic expression 31 can be set for each section. Thus, it is not necessary to obtain a complicated arithmetic expression 31 common to the sections, and the arithmetic expression 31 can be easily set.

In the example of FIG. 3, the arithmetic expression 31 is set so as to pass through the point $(x_1, y_1)$ and the point $(x_2, y_2)$ in the (+) section between at least (−/+) and (+/++). In FIG. 3, an example in which the arithmetic expression 31 set for the (+) section is also applied for the (−) section less than the point $(x_1, y_1)$ and the (++) section larger than the point $(x_2, y_2)$ is shown. For the (−) section and the (++) section, a function with a slope different from the (+) section may be set.

Figure 4:
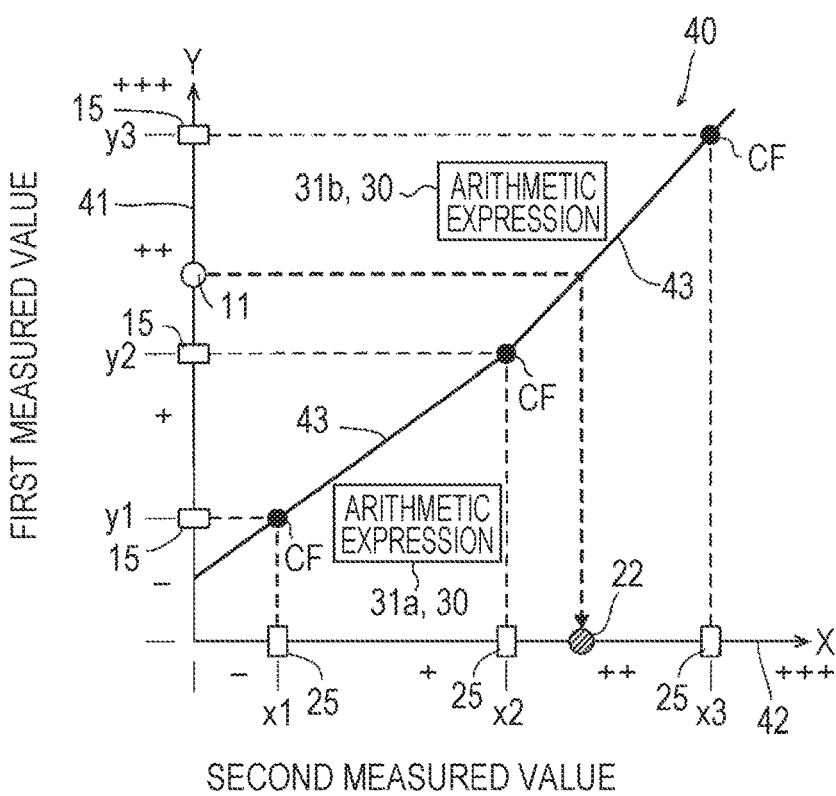
FIG. 4 is a diagram showing an example of an arithmetic expression in the case of three cut-offs.

FIG. 4 shows an example of three pairs of the first cut-off value 15 and the second cut-off value 25 corresponding to the first cut-off value 15. In FIG. 4, the qualitative determination is performed in four stages of (−, +, ++, +++). The first set is the cut-off value $(x_1, y_1)$ of (−/+), the second set is a cut-off value $(x_2, y_2)$ of (+/++), and the third set is a cut-off value $(x_3, y_3)$ of (++/+++).

In the example of FIG. 4, a first arithmetic expression 31a is set so as to pass through the point $(x_1, y_1)$ and the point $(x_2, y_2)$ in the (+) section between at least (−/+) and (+/++). A second arithmetic expression 31b is set so as to pass through the point $(x_2, y_2)$ and the point $(x_3, y_3)$ in the (++) section between at least (+/++) and (++/+++). In FIG. 4, an example in which the first arithmetic expression 31a is applied for the (+) section and the (−) section and the second arithmetic expression 31b is applied for the (++) section and the (+++) section is shown. For the (−) section less than the point $(x_1, y_1)$ and the (+++) section larger than the point $(x_3, y_3)$, a function with a slope different from the (+) section and (++) section may be set.

Figure 5:
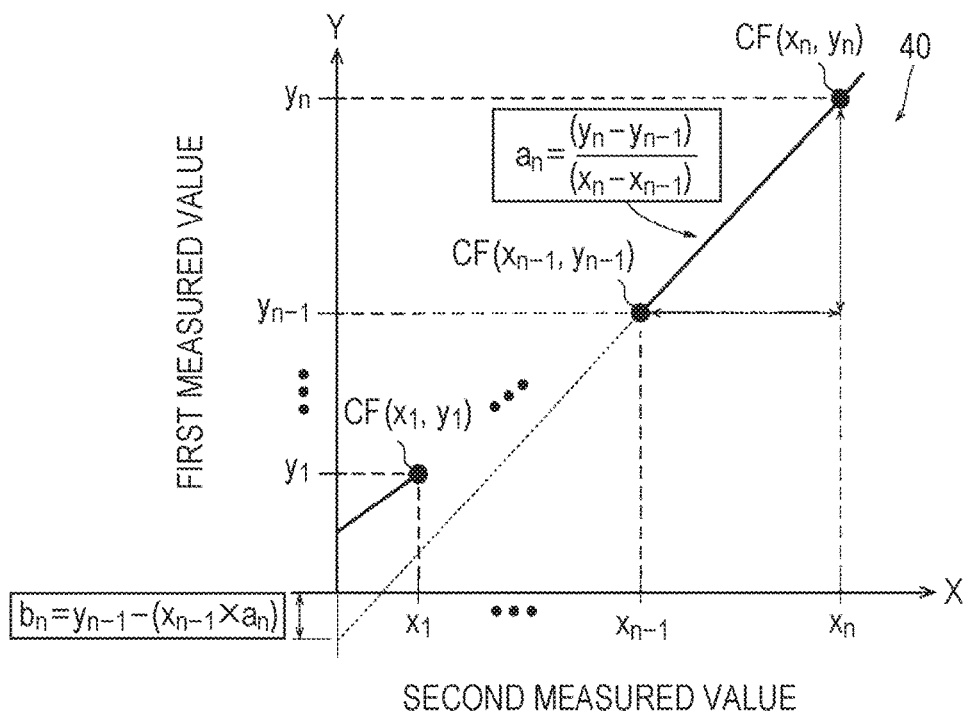
FIG. 5 is a diagram showing slopes and intercepts of an arithmetic expression when there are cut-offs at n points.

The examples in FIGS. 3 and 4 will be generally described. As shown in FIG. 5, the first cut-off values 15 are $y_1, \ldots, y_n$ (n is an integer of 2 or more), and the second cut-off values 25 corresponding to the first cut-off values 15 $(y_1, \ldots, y_n)$ are $x_1, \ldots, x_n$, respectively. At this time, the arithmetic information 30 includes an arithmetic expression 31 represented by the following formula (1) (formula (3)) for each section in which the first measured value Y is $y_{n-1}$ or more and $y_n$ or less.

$$Y'=(Y-b_n)/a_n \qquad (1)$$

wherein Y' is an arithmetic value 22, and Y is a first measured value 11, and $a_n=(y_n-y_{n-1})/(x_n-x_{n-1})$, and $b_n=y_{n-1}-(x_{n-1} \times a_n)$.

According to the above formula (1), the arithmetic expression 31 is set as a function representing a straight line passing through two points defined by two pairs of the first cut-off value 15 and the second cut-off value 25 defining both ends of the section. In other words, the arithmetic expression 31 for each section can be determined only by two pairs of the first cut-off value 15 and the second cut-off value 25 defining both ends of the section. This makes it possible to easily obtain the arithmetic expression 31 for each section.

Figure 6:
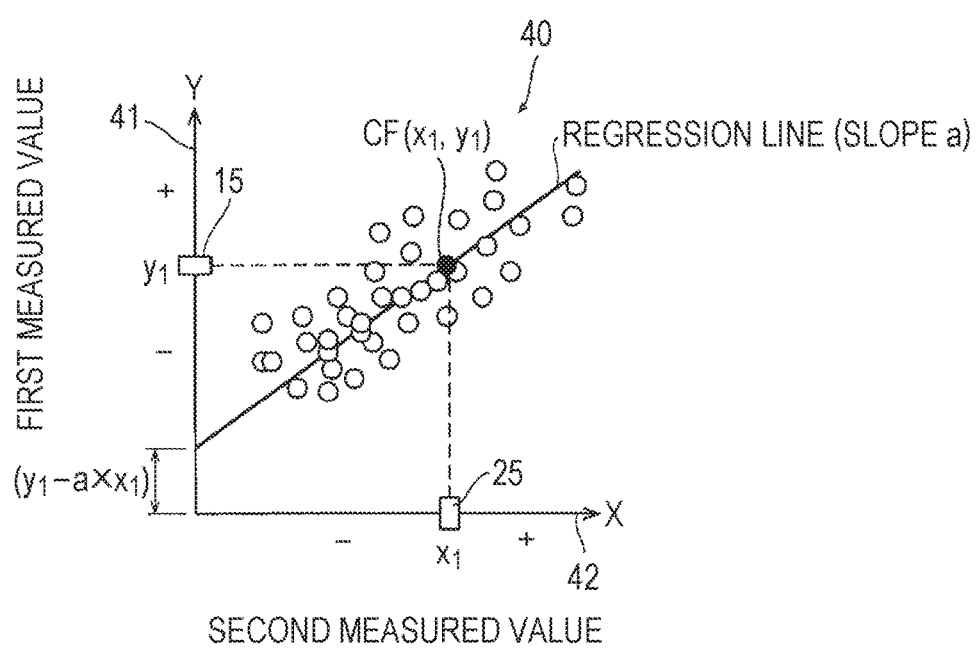
FIG. 6 is a diagram showing an example of an arithmetic expression in the case of one cut-off.

FIG. 6 shows an example in the case where there is one pair of the first cut-off value 15 and the second cut-off value 25 corresponding to the first cut-off value 15 in this embodiment. In the example of FIG. 6, the arithmetic information 30 is set as an arithmetic expression 31 passing through a point determined by one set of the first cut-off value 15 and the second cut-off value 25.

Specifically, when the first cut-off value 15 is $y_1$ and the second cut-off value 25 is $x_1$, the arithmetic information 30 includes an arithmetic expression 31 represented by the following formula (2) (formula (4)).

$$Y'=(Y-y_1)/a+x_1 \qquad (2)$$

wherein Y' is an arithmetic value 22, Y is a first measured value 11, and a is a is a slope of the approximate straight line of a plurality of the first measured values 11 obtained using a first measurement reagent 10 using a plurality of biological samples, and a plurality of the second measured values 21 obtained using a second measurement reagent 20 using the same sample as the plurality of biological samples. The slope a can be acquired by obtaining a regression line from the distribution of each plot in the correlation diagram of FIG. 6.

In this way, in the case where the point determined by the first cut-off value 15 and the second cut-off value 25 is one point, there are numerous straight lines passing through the point $(x_1, y_1)$. Thus, the arithmetic expression 31 can be set by adopting the slope a of the regression line obtained from the data of a plurality of sets of the first measured value 11 and the second measured value 21 under the condition of passing through the point $(x_1, y_1)$.

This makes it possible to easily obtain the arithmetic expression 31 as a function of the approximate straight line passing through the point $(x_1, y_1)$ determined by the first cut-off value 15 and the second cut-off value 25.

[Method for Obtaining Arithmetic Expression]

Next, a method for obtaining an arithmetic expression will be described. The method for obtaining an arithmetic expression of this embodiment is a method of obtaining an arithmetic expression 31 for operating a measured value obtained by measuring a test substance 90 contained in a biological sample based on a predetermined measurement principle.

The method of obtaining an arithmetic expression 31 includes at least the following steps. (A) acquiring a first cut-off value 15 for a first measured value 11 of a test substance 90 obtained using a first measurement reagent 10. (B) acquiring a second cut-off value 25 for a second measured value 21 of the test substance 90 obtained by using a second measurement reagent 20. (C) acquiring a function for matching an arithmetic value 22 of the first cut-off value 15 with the second cut-off value 25, based on the first cut-off value 15 and the second cut-off value 25, as an arithmetic expression 31 of the measured value obtained using the first measurement reagent 10 and the measured value obtained using the second measurement reagent 20. Step (A) and step (B) are in any order.

In step (A), the first cut-off value 15 is a value preset for the first measurement reagent 10 and can be acquired as reagent information of the first measurement reagent 10. In step (B), the second cut-off value 25 is a value preset for the second measurement reagent 20 and can be acquired as reagent information of the second measurement reagent 20.

In step (C), the arithmetic expression 31 is obtained as a function for matching the arithmetic value 22 of the first cut-off value 15 with the second cut-off value 25, based on at least the acquired first cut-off value 15 and the second cut-off value 25.

As shown in FIGS. 3 to 6, this makes it possible to obtain an arithmetic expression 31 for operating the first measured value 11 obtained using the first measurement reagent 10 to a value obtained using the second measurement reagent 20 so as to match the first cut-off value 15 with the second cut-off value 25 before and after operation with each other. Therefore, by using the obtained arithmetic expression 31, the clinical judgment based on the first measured value 11 and the first cut-off value 15 and the clinical judgment based on the arithmetic value 22 and the second cut-off value 25 can be matched with each other. As a result, it is possible to suppress change in clinical judgment before and after operation, when operating the measured value obtained under the measurement condition using the first measurement reagent 10 to the value when measured under the measurement condition using the second measurement reagent 20 in clinical examination.

In the example shown in FIG. 3, a first coordinate axis 41 representing the first measured value 11 obtained using the first measurement reagent 10 and a second coordinate axis 42 representing a second measured value 21 obtained using the second measurement reagent 20 are set. In FIG. 3, a coordinate plane 40 is set with the first coordinate axis 41 as the Y axis and the second coordinate axis 42 as the X axis.

Then, the arithmetic expression 31 is obtained as a function of a straight line passing through the point (x, y) determined by first cut-off value y on the first coordinate axis 41 and second cut-off value x on the second coordinate axis 42.

That is, the straight line passing through the point (x, y) on the coordinate plane 40 is set as y=ax+b. At this time, assuming that the first measured value 11 is Y and the arithmetic value 22 is Y', Y'=x, thus Y=aY'+b. When this function is solved for Y', Y'=(Y−b)/a.

Therefore, as shown in FIGS. 3 to 5, when there are a plurality of pairs of the first cut-off value 15 and the second cut-off value 25 corresponding to the first cut-off value 15, the above formula (1) is derived. As shown in FIG. 6, when there is one pair of the first cut-off value 15 and the second cut-off value 25 corresponding to the first cut-off value 15, the above formula (2) is derived.

This makes it possible to easily obtain an arithmetic expression 31 that prevents the clinical judgment from changing before and after operation by a straight line passing through the point (x, y) on the coordinate plane 40 between the first coordinate axis 41 and the second coordinate axis 42.

[Configuration Examples of Measuring Apparatus]

Figure 7:
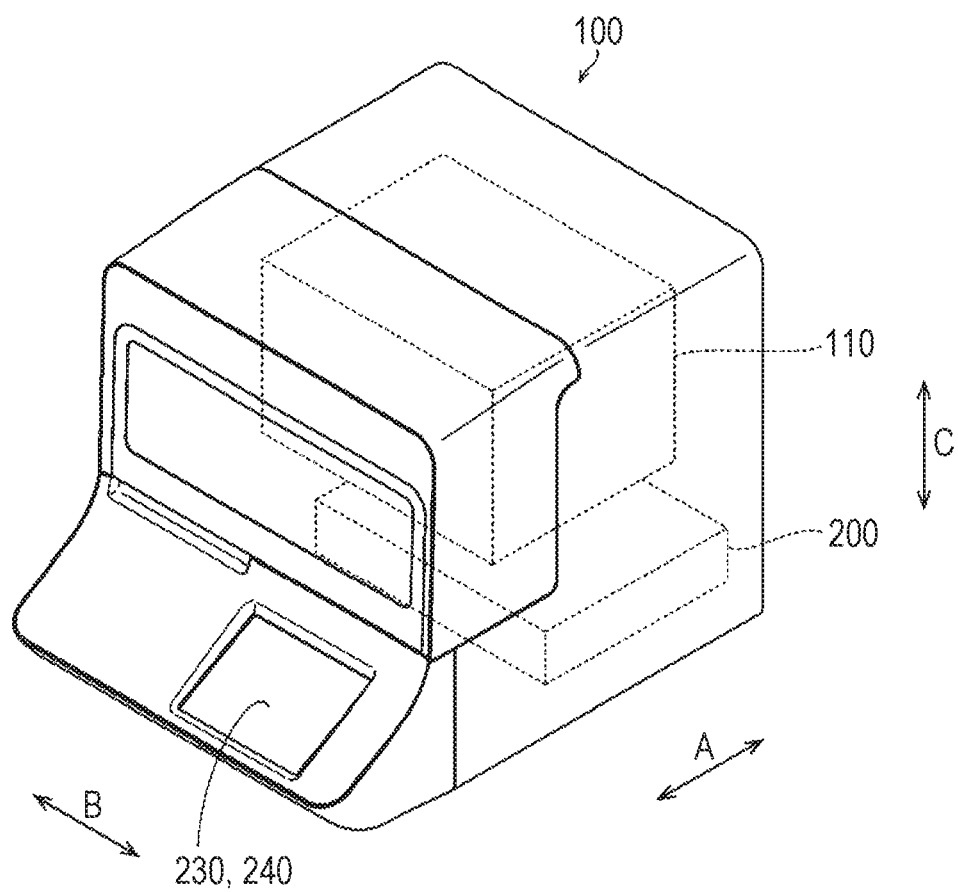
FIG. 7 is a perspective view showing a configuration example of a measuring apparatus.

FIG. 7 shows an example of a specific apparatus configuration of a measuring apparatus 100. In FIG. 7, the measuring apparatus 100 is a gene amplification measuring apparatus. The gene amplification measuring apparatus amplifies a target gene that is a test substance 90 using a measurement reagent and acquires a measured value by detecting the amplified target gene. In the fields where there are many unknown aspects and accumulation of academic knowledge is required, like genetic testing, the development of measurement reagents is also active. On the other hand, it is desirable to enable comparison of measured values using different measurement reagents. Therefore, the measuring apparatus 100 according to this embodiment is useful when applied to a gene amplification measuring apparatus.

In the example of FIG. 7, the measurement method performed by the measuring apparatus 100 is a method of measuring at least one of the amount of a nucleic acid as the test substance 90 and the expression level of the nucleic acid. Thereby, for example, in the genetic testing, a first measured value 11 using a first measurement reagent 10 for a specific examination item can be operated to an arithmetic value 22 using other second measurement reagent 20 without changing the qualitative determination.

In the example of FIG. 7, the measurement method performed by the measuring apparatus 100 includes a step of amplifying a nucleic acid using the first measurement reagent 10. Thereby, by operating the first measured value 11 of the nucleic acid amplified using the first measurement reagent 10 to obtain the arithmetic value 22, it becomes possible to compare with the measured value of the nucleic acid amplified using the second measurement reagent 20. The nucleic acid amplification method in the step of amplifying a nucleic acid is not particularly limited, and examples thereof include a PCR (polymerase chain reaction) method, a LAMP (Loop-mediated Isothermal Amplification, Eiken Chemical Co., Ltd.) method, and the like.

In the example of FIG. 7, amplification by the LAMP method is performed in the step of amplifying a nucleic acid. The LAMP method has advantages that amplification efficiency is high and the amplification reaction can proceed isothermally. This makes it possible to quickly perform the processing of amplifying the nucleic acid using the first measurement reagent 10, measuring at least one of the amount of the nucleic acid and the expression level of the nucleic acid, and acquiring the first measured value 11. As a result, the time taken from the start of the measurement on the examination item until the arithmetic value 22 of the first measured value 11 is obtained and can be compared with the measurement result using the other second measurement reagent 20 is shortened, and prompt clinical examination becomes possible.

In the example of FIG. 7, the measurement method performed by the measuring apparatus 100 acquires the first measured value 11 corresponding to the amount of the test substance 90 in the sample, based on the turbidity change of the sample due to the amplification of the nucleic acid using the first measurement reagent 10. In the LAMP method, magnesium pyrophosphate is produced as a byproduct in the process of the amplification reaction, and white turbidity occurs in the sample depending on the amount of magnesium pyrophosphate produced. Therefore, by measuring the turbidity from the scattered light intensity of the sample and the intensity ratio of transmitted light and scattered light, the result of the amplification reaction can be measured. It is known that a linear relationship is established between the nucleic acid concentration to be amplified and the time from the start of the reaction until the turbidity exceeds a predetermined threshold. Thus, a calibration curve is prepared from a sample (calibrator) containing a nucleic acid of a known concentration, and based on the prepared calibration curve, the amount (concentration) of the nucleic acid in the measurement sample can be calculated. This makes it possible to easily acquire the first measured value 11 based on turbidity change.

In addition, the measuring apparatus in FIG. 7 is an apparatus that supports diagnosis of cancer metastasis in excised tissue in cancer surgery. That is, qualitative determination is to determine the degree of suspicion for the presence or absence of cancer metastasis. The qualitative determination to determine the degree of suspicion for the presence or absence of cancer metastasis is positive with suspicion of metastasis, negative without suspicion of metastasis, or the like. Since the judgment on the presence or absence of metastasis in cancer treatment is highly important, the measurement method and the measuring apparatus 100 that implements the measurement method according to this embodiment are particularly useful in that those can suppress change in the qualitative determination on clinical judgment of high importance like the presence or absence of cancer metastasis before and after operation of the first measured value 11.

The measuring apparatus 100 is configured so as to amplify a cancer-derived gene (mRNA) present in the excised tissue by using the LAMP method, measure (detect) the turbidity of a solution generated along with the amplification of the gene, and acquire the first measured value 11 based on turbidity change.

That is, in the example of FIG. 7, the test substance 90 is a nucleic acid whose expression level increases or decreases in cancer cells as compared with in normal cells. This makes it possible to acquire the first measured value 11 and the arithmetic value 22 for performing clinical judgment such as the presence or absence of cancer metastasis, using the nucleic acid that is the test substance 90 as a marker gene.

More specifically, the test substance 90 is mRNA of cytokeratin 19 (CK19). Thereby, by using mRNA of CK19 suitable as a marker as the test substance 90 since the expression level is high in the metastasis-positive lymph node and the expression level is low in the metastasis-negative lymph node and the individual difference is small in the expression level, clinical judgment on the presence or absence of cancer metastasis and the like can be performed with high accuracy.

As shown in FIG. 7, the measuring apparatus 100 includes a measurement unit 110 and a control unit 200. As will be described later, the control unit 200 includes an operational unit 120.

Figure 8:
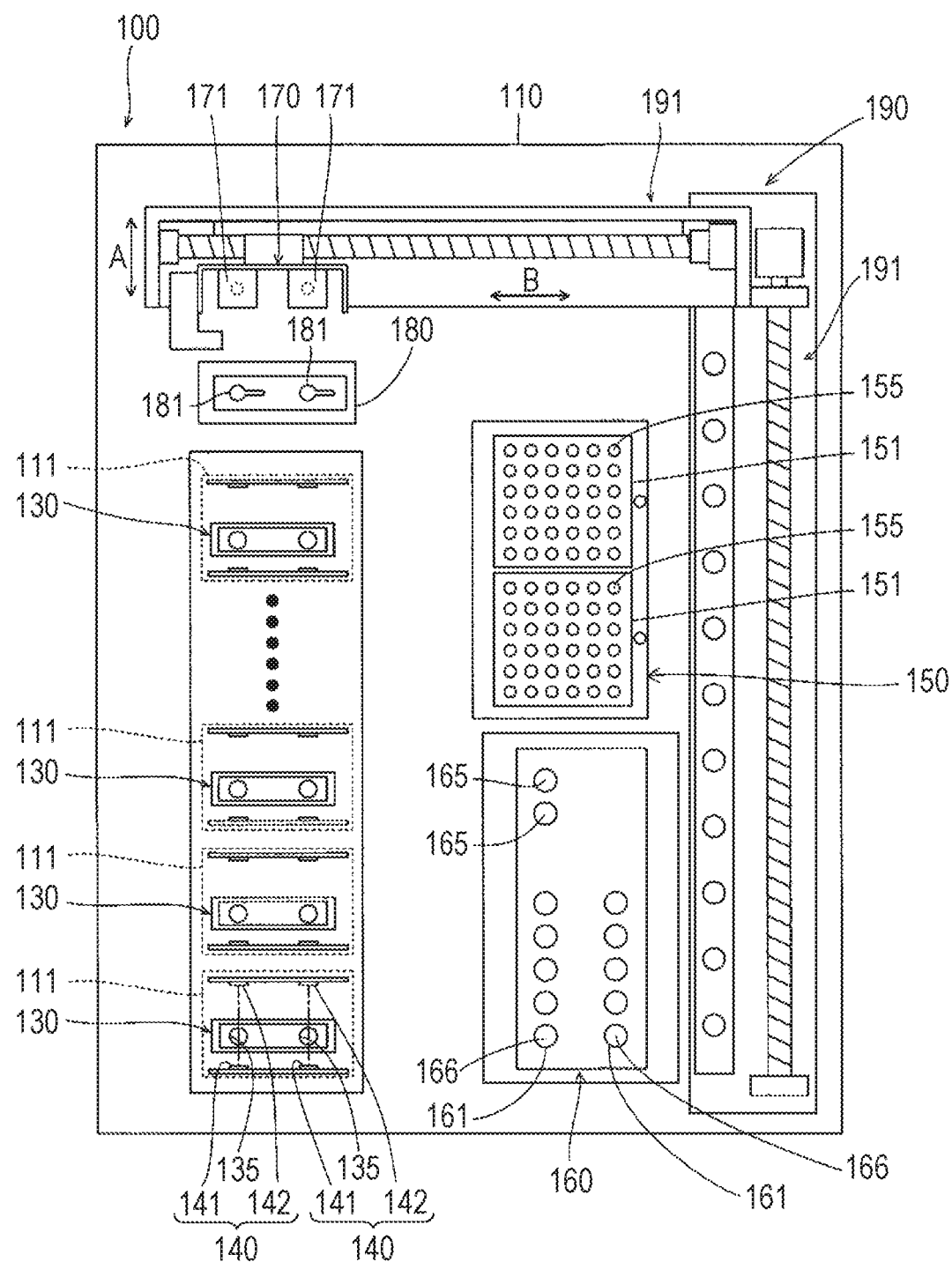
FIG. 8 is a plan view showing a configuration example of a measurement unit of the measuring apparatus shown in FIG. 7.

The measurement unit 110 performs measurement processing for acquiring the first measured value 11 reflecting the amount of the test substance 90 using the first measurement reagent 10. As shown in FIG. 8, the measurement unit 110 includes a reaction section 130 for amplifying a nucleic acid using the first measurement reagent 10. Thereby, by operating the first measured value 11 of the nucleic acid amplified using the first measurement reagent 10 to obtain the arithmetic value 22, it becomes possible to compare with the measured value of the nucleic acid amplified using the second measurement reagent 20.

The measurement unit 110 includes a turbidity detection section 140 that detects a turbidity of a sample containing the test substance 90, and the first measured value 11 corresponding to the amount of the test substance 90 in the sample is acquired, based on the turbidity change of the sample due to the amplification of the nucleic acid using the first measurement reagent 10. This makes it possible to easily acquire the first measured value 11 based on turbidity change.

In addition, the measurement unit 110 shown in FIG. 8 includes a tip placement section 150, a liquid container placement section 160, a dispensing section 170, and a tip disposal section 180.

The tip placement section 150 is a setting position for setting a tip container 151 storing a plurality of pipette tips 155. Two tip containers 151 are set in the tip placement section 150.

Various liquid storage containers storing predetermined liquids are placed on the liquid container placement section 160. The liquid container placement section 160 is provided with a container setting hole 161 capable of storing a liquid container. In the liquid container placement section 160, a reagent container 165 storing the first measurement reagent 10 is set. A sample container 166 storing a solubilized extract prepared by applying a treatment such as homogenization, filtration and dilution to the excised tissue in advance, as a biological sample, is set in the liquid container placement section 160. The sample container 166 is set in a pair of a container for storing an undiluted biological sample and a container for storing a diluted sample in which the biological sample is diluted, for the same biological sample.

In the example of FIG. 8, the measurement unit 110 is provided with a plurality of reaction detection blocks 111 having the reaction section 130 and the turbidity detection section 140. Thereby, the measurement unit 110 can perform measurement on a plurality of biological samples in parallel. Since the configuration of each reaction detection block 111 is the same, only one reaction detection block 111 will be described. Two detection cells 135 can be set in the reaction section 130. The detection cell 135 is a reaction container for mixing the biological sample and the first measurement reagent 10. The reaction section 130 can heat the sample in the detection cell 135 to a predetermined temperature by a Peltier element (not shown) or the like.

The turbidity detection section 140 includes a light emitting part 141 and a light receiving part 142. The light emitting part 141 includes, for example, an LED light source that irradiates blue (wavelength: 465 nm) light, and the light receiving part 142 includes, for example, a photodiode. In the reaction detection block 111, two turbidity detection sections 140 are arranged, so as to measure each of the two detection cells 135 set in the reaction section 130. The light emitting part 141 irradiates the detection cell 135 with light, and the light passing through the detection cell 135 is received by the light receiving part 142. The measuring apparatus 100 is configured to detect the presence or absence of the detection cell 135 based on the received light intensity, and also detect and monitor the turbidity of the liquid stored in the detection cell 135 in real time.

The dispensing section 170 is configured to dispense the first measurement reagent 10 and the biological sample set in the liquid container placement section 160 into the detection cells 135 set in the respective reaction detection blocks 111. The dispensing section 170 includes two syringe parts 171 for dispensing liquid.

The dispensing section 170 is moved in the horizontal direction and the vertical direction inside the measurement unit 110 by a moving mechanism 190. In FIGS. 7 and 8, the moving mechanism 190 is configured by a combination of a plurality of linear motion mechanisms 191 for movement to directions, directions A and B orthogonal to each other in the horizontal plane and in the vertical direction (direction C). The linear motion mechanism 191 is configured by, for example, a motor, a driving force transmission mechanism such as a ball screw-ball nut and a belt-pulley, a linear motion guide such as a linear guide, and the like. The linear motion mechanism 191 in the vertical direction is not shown. The dispensing section 170 detachably attaches the pipette tip 155 set on the tip placement section 150 to the syringe part 171 by the moving mechanism 190. The dispensing section 170 sucks the liquid in the reagent container 165 and the sample container 166 set in the liquid container placement section 160 via the attached pipette tip 155. The dispensing section 170 dispenses the sucked liquid into the detection cells 135 set in the reaction detection block 111. By means of the two syringe parts 171, liquid dispensing can be performed simultaneously to two detection cells 135 set in the reaction detection blocks 111.

After dispensing, the dispensing section 170 moves to the upper side of the tip disposal section 180 and discards the used pipette tip 155. Two tip disposal holes 181 for discarding the used pipette tips 155 from the two syringe parts 171 are provided in the tip disposal section 180.

Next, examples of the first measurement reagent 10 and the second measurement reagent 20 will be described. The first measurement reagent 10 and the second measurement reagent 20 used for the measurement of the measuring apparatus 100 shown in FIG. 8 include a reagent for amplifying mRNA of CK19 by the LAMP method. In addition, the first measurement reagent 10 and the second measurement reagent 20 are configured as a reagent kit composed of a plurality of reagent solutions. FIG. 9 shows composition examples of the first measurement reagent 10 and the second measurement reagent 20. In detail, the first measurement reagent 10 and the second measurement reagent 20 contain a primer reagent containing a plurality of primers corresponding to the target region to be amplified, dNTPs (deoxynucleotide triphosphate including dATP, dCTP, dGTP, and dTTP) to be a substrate of complementary strand synthesis, and magnesium sulfate ($MgSO_4$). In the example of FIG. 9, the primer reagent contains six types of primers with different target regions. In addition, the first measurement reagent 10 and the second measurement reagent 20 contain an enzyme reagent having an enzyme activity for amplifying a nucleic acid. The reagent container 165 storing the primer reagent and the reagent container 165 storing the enzyme reagent are set at predetermined positions of the liquid container placement section 160 in FIG. 8.

As can be seen from FIG. 9, the first measurement reagent 10 and the second measurement reagent 20 are reagents containing the same components because they react under the same measurement principle, but the proportions of the components contained are different. That is, the first measurement reagent 10 and the second measurement reagent 20 act on the same measurement principle and have compositions different from each other. Thereby, since the first measurement reagent 10 and the second measurement reagent 20 are basically the same kind of reagents acting on the same measurement principle, not a reagent acting on a completely different measurement principle, high correlation is recognized also between the measured values, thus operation using the arithmetic information 30 can be performed with high accuracy.

Figure 10:
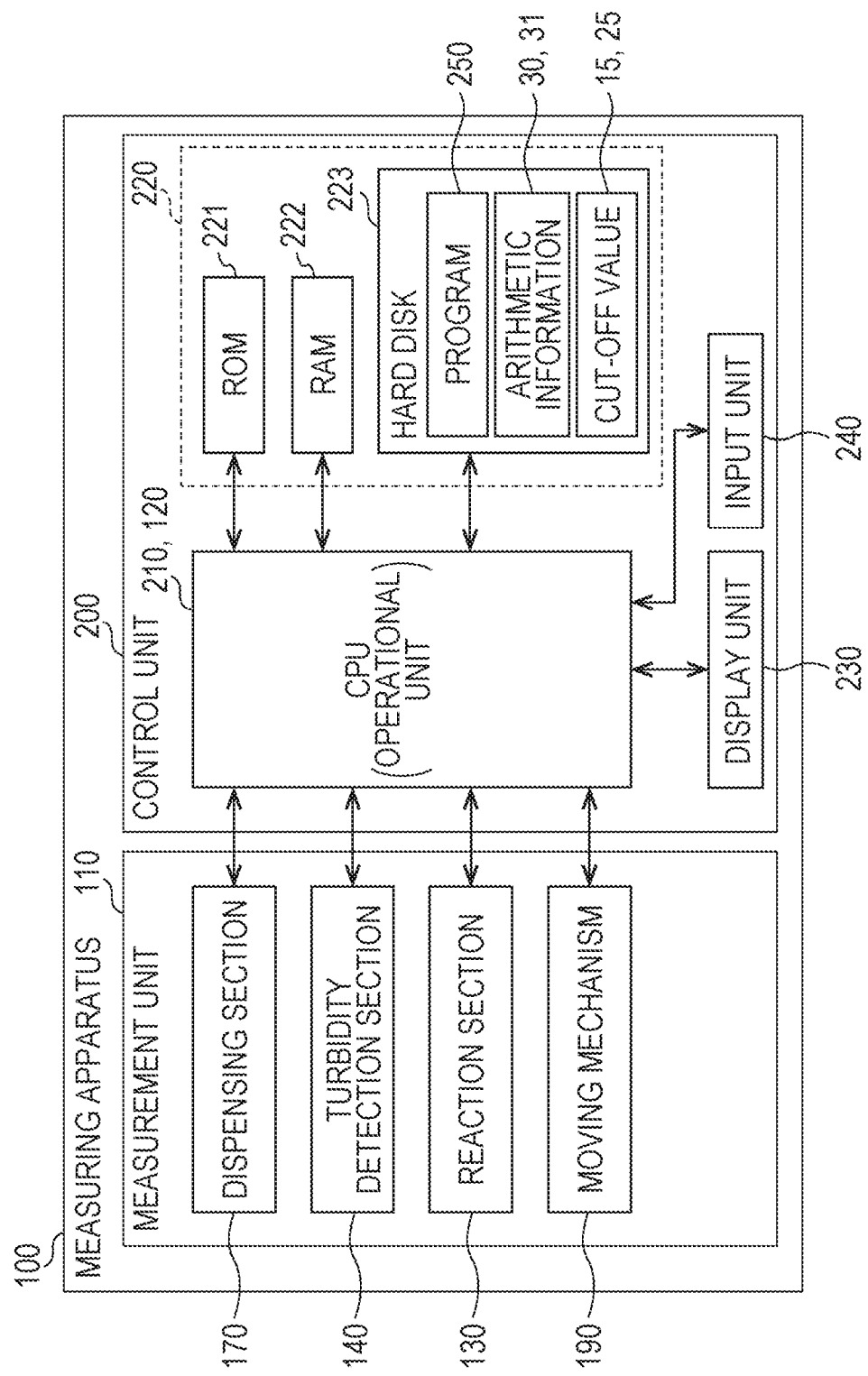
FIG. 10 is a block diagram showing a configuration example of a control unit of the measuring apparatus shown in FIG. 7.

FIG. 10 shows a configuration example of a control unit 200 of the measuring apparatus 100. In FIG. 10, the control unit 200 is a computer including a CPU 210 and a storage unit 220. Further, the measuring apparatus 100 includes a display unit 230 and an input unit 240. The storage unit 220 includes a ROM 221, a RAM 222, and a hard disk 223. The storage unit 220 may include a rewritable nonvolatile storage device other than the hard disk 223.

The CPU 210 executes a computer program stored in the ROM 221 and a computer program loaded in the RAM 222. The RAM 222 is used for reading the computer program recorded in the ROM 221 and the hard disk 223. The RAM 222 is also used as a work area of the CPU 210 when executing these computer programs.

In the hard disk 223, various computer programs to be executed by the CPU 210, such as an operating system and an application program, and data used for executing a computer program are stored.

In the configuration example of FIG. 10, a program 250 for executing the measurement method of this embodiment is stored in the hard disk 223. That is, the program 250 is a program for measuring a test substance 90 contained in a biological sample based on a predetermined measurement principle, which makes a computer acquire a first measured value 11 of the test substance 90 measured using a first measurement reagent 10, makes the computer acquire arithmetic information 30 designed to make a first cut-off value 15 for the measured value obtained using the first measurement reagent 10 correspond to a second cut-off value 25 for a measured value obtained using a second measurement reagent 20 different from the first measurement reagent 10, and makes the computer operate the first measured value 11 to an arithmetic value 22 when measured using the second measurement reagent 20, using the arithmetic information 30.

In this embodiment, by making the CPU 210 execute the program 250, the first measured value 11 obtained using the first measurement reagent 10 can be operated to an arithmetic value 22 when measured using a second measurement reagent 20, under the condition that the first cut-off value 15 and the second cut-off value 25 are associated with each other, using the arithmetic information 30. In other words, in the case of operating using a regression equation obtained from the measurement result obtained by measuring the same specimen using each of the first measurement reagent 10 and the second measurement reagent 20, the arithmetic value is determined irrespective of the cut-off value. However, according to the arithmetic information 30 in which the cut-off values are made to correspond to each other, the arithmetic value 22 can be determined so that the relationship between the first measured value 11 and the first cut-off value 15 is maintained in the relationship between the arithmetic value 22 and the second cut-off value 25 as it is. As a result, it is possible to suppress change in clinical judgment before and after operation, when operating the measured value obtained using the first measurement reagent 10 to the value in the case of using the second measurement reagent 20 in clinical examination.

In other words, in the configuration example of FIG. 10, the CPU 210 executes the program 250 to function as the operational unit 120 of the measuring apparatus 100.

In the configuration example of FIG. 10, the arithmetic information 30 is recorded in the storage unit 220 in advance. The operational unit 120 operates the first measured value 11 to the arithmetic value 22 by the arithmetic information 30 recorded in the storage unit 220. In this way, it is not necessary to acquire the arithmetic information 30 from the outside, and operation can be easily performed by previously storing the arithmetic information 30 in the storage unit 220.

In the storage unit 220, a cut-off value for performing the qualitative determination is recorded in advance. In this embodiment, since the qualitative determination result using the first measured value 11 and the first cut-off value 15 and the qualitative determination result using the arithmetic value 22 and the second cut-off value 25 can be matched with each other, at least one of the first cut-off value 15 and the second cut-off value 25 may be stored in the storage unit 220 as the cut-off value. For example, in one example, the storage unit 220 stores the first cut-off value 15 and does not store the second cut-off value 25. In another example, the storage unit 220 does not store the first cut-off value 15 and stores the second cut-off value 25. In another example, the storage unit 220 stores both the first cut-off value 15 and the second cut-off value 25.

The CPU 210 is connected to each unit of the display unit 230, the input unit 240 and the measurement unit 110, via an I/O interface (not shown). Thereby, the CPU 210 receives signals from these mechanisms connected via the I/O interface, and the CPU 210 also controls these mechanisms.

The display unit 230 displays images to present information to the operator. The input unit 240 receives an input from the operator. In the configuration example shown in FIG. 7, the display unit 230 and the input unit 240 are configured as a single display input unit by a touch panel type display. The display unit 230 and the input unit 240 may be separately configured by a display device such as a liquid crystal display and an input device such as a mouse or a keyboard.

Figure 11:
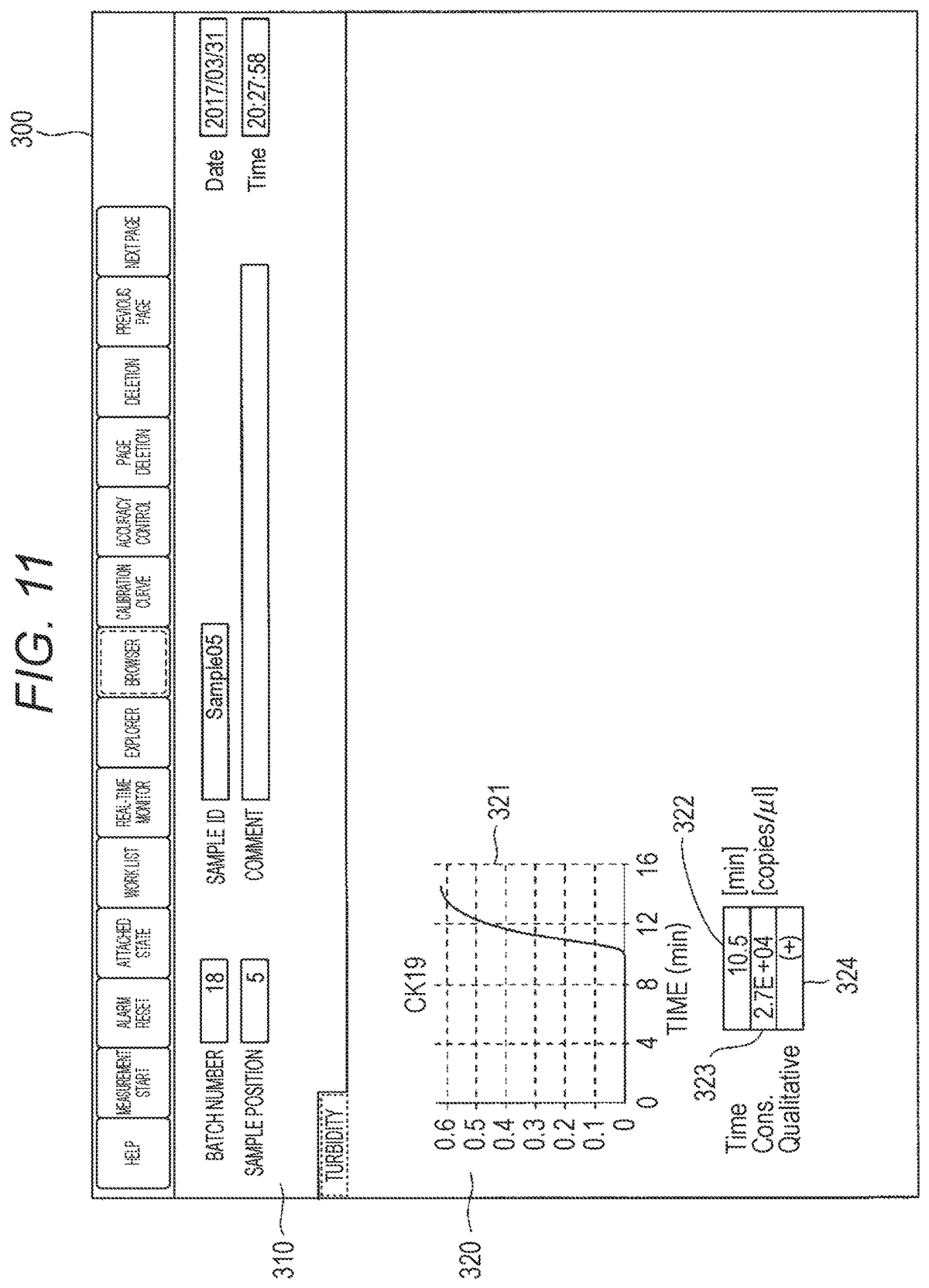

The CPU 210 displays on the display unit 230, for example, the measurement result display screen 300 shown in FIG. 11 and the measurement result display screen 350 shown in FIG. 12.

In the example of FIG. 11, the measurement result display screen 300 is provided with a sample information area 310 for displaying various kinds of information on the biological sample and a measurement result area 320 for showing the measurement result of the biological sample displayed in the sample information area 310.

In the example of FIG. 11, in the sample information area 310, the batch number indicating the order of the batch processing, the sample ID of the biological sample, the sample set position where the biological sample is set, the comments on the biological sample and the diluted sample, the measurement date and time and the like are displayed.

The measurement result area 320 is provided with a graph column 321 showing the relationship between the turbidity of the biological sample and time (min), an amplification rise time display column 322, a measured value display column 323, and a determination result display column 324.

In the amplification rise time display column 322, a time ("10.5" (min) in the screen) corresponding to 0.1 of the turbidity that is the vertical axis of the graph column 321 is displayed.

In the measured value display column 323, the concentration or concentration range ("2.7E+04" in the screen) (copies/µl) of the test substance 90 calculated from the rise time is displayed.

Figure 13:
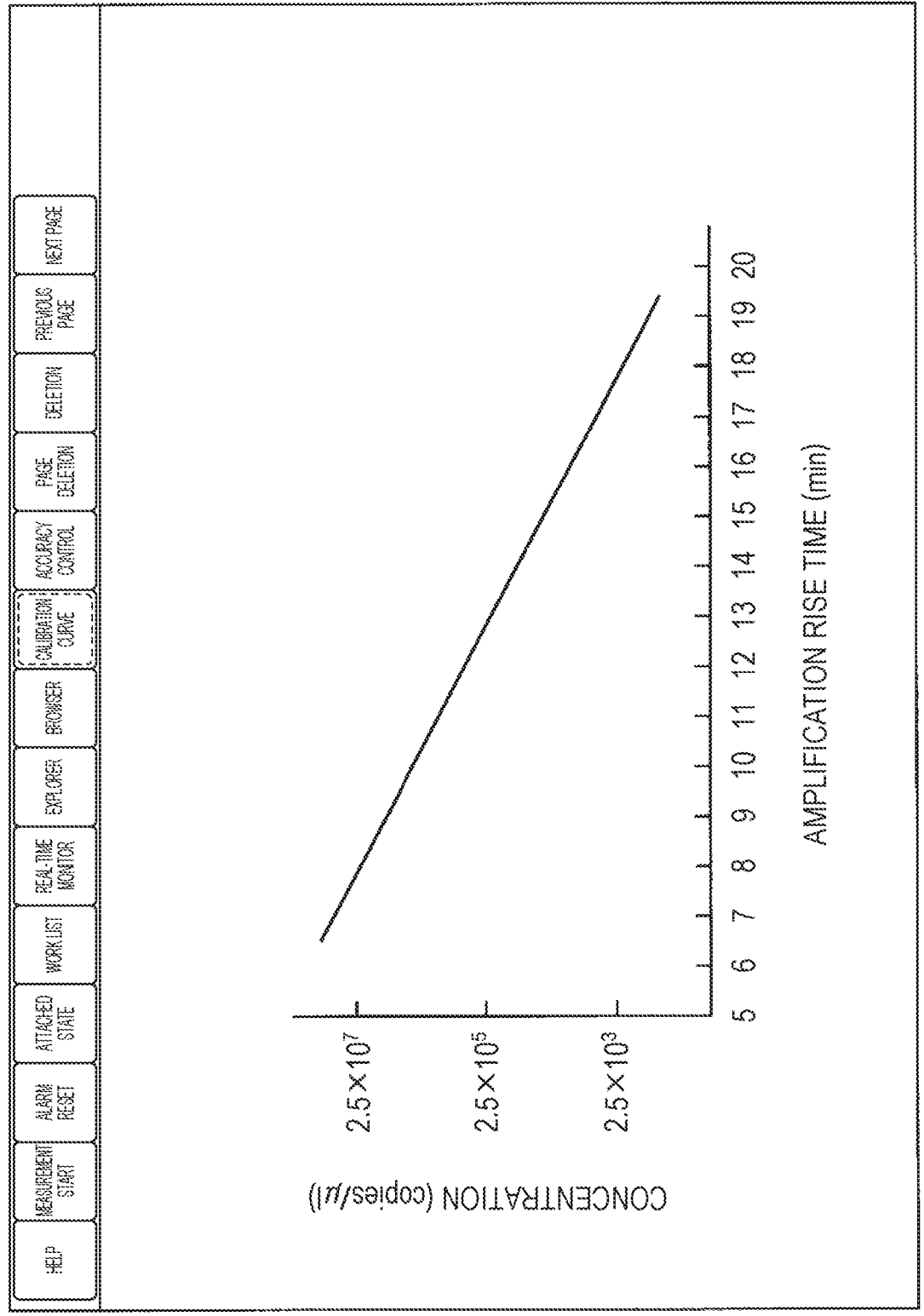
FIG. 13 is a diagram showing an example of a calibration curve.

Specifically, the concentration of the test substance 90 is calculated from the amplification rise time (=10.5), based on the calibration curve (see FIG. 13) that is a linear function of the amplification rise time and the concentration prepared by the calibrator measured in advance. When the concentration falls within the range of the linearity guarantee of the calibration curve, the actual measured concentration is displayed, and when the concentration is out of the range of the linearity guarantee, a display indicating that it is out of the range of the linearity guarantee is made. The calibration curve shown in FIG. 13 is acquired by measuring a plurality of calibrators with known concentrations in advance before the start of the measurement and measuring the amplification rise time corresponding to 0.1 of the turbidity.

The result of the qualitative determination (positive "(+)", negative "(−)") on whether or not the target gene (mRNA) is present in the biological sample by the cut-off value or more is displayed in the determination result display column 324. When the measurement result measured using the biological sample is negative despite the positive result of the measurement result measured using the diluted sample in which the biological sample is diluted, "(+)I" indicating that amplification inhibition may have occurred is displayed. When the cut-off value of (+/++) and the cut-off value of (++/+++) are set, the qualitative determination results of (++) and (+++), in addition to (+), (−), are displayed. When the cut-off value of (+/++) and the cut-off value of (++/+++) are set, (−) indicates negative, (+) indicates positive, (++) indicates strong positive, and (+++) indicates stronger strong positive. In the qualitative determination result, it is judged that there is no suspicion of disease (negative) or there is suspicion of disease (positive) with (−) or (+) or more. (+), (++), (+++) indicate the degree of suspicion of disease. In other words, in positives of (+) or more, the greater the number of "+", the stronger the suspicion of disease. Here, the suspicion of disease is a suspicion about the presence or absence of cancer metastasis.

In the configuration example of FIG. 11, the measuring apparatus 100 displays at least one of an arithmetic value 22 and a first measured value 11 on a display unit 230. That is, either one or both of the arithmetic value 22 and the first measured value 11 can be displayed in a measured value display column 323. Whether to display either of the arithmetic value 22 or the first measured value 11 or both of them can be set, for example, by an input operation via an input unit 240. For example, when a user using the second measurement reagent 20 newly introduces the first measurement reagent 10, the arithmetic value 22 can be displayed for matching the measurement result by the second measurement reagent 20. When there is no data accumulation using the second measurement reagent 20, the first measured value 11 may be displayed. FIG. 11 shows an example of displaying the arithmetic value 22.

FIG. 12 shows an example of a measurement result display screen 350 displaying a plurality of measurement results in a table format. The measurement result display screen 350 is provided with a sample information area 360 for displaying various kinds of information on the biological sample and a measurement result area 370 for showing the measurement result of the biological sample displayed in the sample information area 360.

The sample information area 360 includes a measurement date column 361, a time column 362, a sample ID column 363, and a carcinoma column 364. Thereby, for each sample in the sample information area 360, the measurement execution date and the measurement execution time, the sample ID of the measured biological sample, and the carcinoma of the sample are displayed. The carcinoma column 364 is a display column for displaying the type of disease and may be referred to as a disease type column. FIG. 12 shows an example in which "BC" representing Breast Cancer is displayed. For other carcinomas, for example, Stomach Cancer is displayed as "SC", Colorectal Cancer is displayed as "CC", and the like.

The measurement result area 370 includes a determination result display column 371 and a measured value display column 372. Thereby, the measurement result area 370 displays the qualitative determination result, and the first measured value 11 or the arithmetic value 22. As a qualitative determination result, the determination result display column 371 includes display 371a of positive (Pos.) or negative (Neg.) indicating the presence or absence of suspected disease and display 371b of (−), (+), (++), (+++) or the like indicating the degree of suspicion of disease. Also in the configuration example of FIG. 12, the measuring apparatus 100 displays at least one of an arithmetic value 22 and a first measured value 11 on a display unit 230. That is, either one or both of the arithmetic value 22 and the first measured value 11 can be displayed in a measured value display column 372. FIG. 12 shows an example of displaying the arithmetic value 22. Whether to display either of the arithmetic value 22 or the first measured value 11 or both of them can be changed by setting.

In the example of FIG. 12, the measurement result display screen 350 displays measurement results of a plurality of biological samples in a table format in chronological order. The measurement result display screen 350 is a screen for displaying a plurality of measurement results as a list side by side, in descending order of measurement execution date and measurement execution time. The arrangement order of the measurement results may be changed for each carcinoma, each determination result (negative, positive, strong positive), or the like.

In this way, in the configuration examples of FIGS. 11 and 12, the measuring apparatus 100 includes a display unit 230 for displaying at least one of the arithmetic value 22 calculated by the operational unit 120 and the first measured value 11 acquired by the measurement unit 110. This makes it possible for the user to confirm at least one of the arithmetic value 22 and the first measured value 11 on the display unit 230. As a result, since the measured value that serves as the basis of the clinical judgment can be easily confirmed, the convenience of the measuring apparatus 100 is improved.

Figure 14:
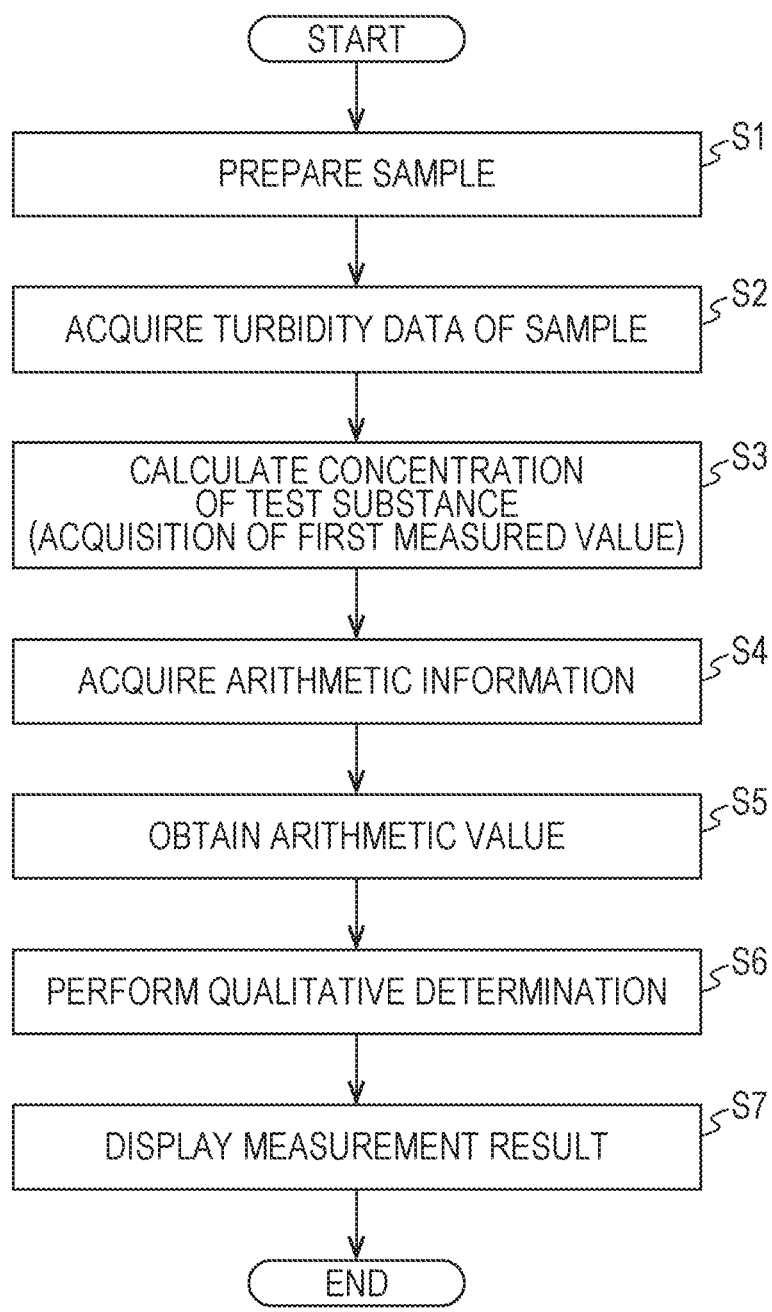
FIG. 14 is a flowchart showing an example of measurement processing of the measuring apparatus.

With reference to FIG. 14, the flow of the measurement processing of the measuring apparatus 100 in the configuration examples shown in FIGS. 7 to 13 will be described. In the configuration example of FIG. 8, badge processing that performs measurement of different biological samples in parallel in each of the plurality of reaction detection blocks 111 is possible, but here, for convenience, measurement processing in one reaction detection block 111 will be described.

When measurement is started, in step S1, a measurement sample is prepared in a detection cell 135. First, under the control of a CPU 210, a dispensing section 170 is moved by a moving mechanism 190, pipette tips 155 of a tip placement section 150 are attached to two syringe parts 171, and a primer reagent is aspirated from a reagent container 165 set in a liquid container placement section 160 and discharged to each of two detection cells 135. Thereafter, under the control of the CPU 210, the pipette tips 155 attached to the syringe parts 171 are discarded.

Likewise, under the control of the CPU 210, the dispensing section 170 attaches the pipette tips 155, an enzyme reagent is aspirated from the reagent container 165 set in the liquid container placement section 160 and discharged to each of the two detection cells 135, and the used pipette tips 155 are discarded. Then, under the control of the CPU 210, the dispensing section 170 attaches the pipette tips 155, and the biological sample and the diluted sample are respectively aspirated from the sample container 166 set in the liquid container placement section 160 and discharged to each of the two detection cells 135, and the used pipette tips 155 are discarded. Thereby, a measurement sample is prepared. The dispensed detection cells 135 are hermetically sealed by a closing mechanism (not shown) provided in the reaction section 130 under the control of the CPU 210.

When the detection cells 135 are sealed, in step S2, the turbidity data of the sample is acquired. Specifically, the detection cells 135 are irradiated with light by the light emitting parts 141 of the turbidity detection sections 140, and the light receiving parts 142 output to the CPU 210 a detection signal corresponding to the amount of received light transmitted through the detection cells 135. The interior of the detection cells 135 are heated to a predetermined reaction temperature by the reaction section 130. The reaction temperature is set to a temperature suitable for the LAMP reaction, and is, for example, about 64° C. to 65° C.

By the LAMP reaction, CK19 mRNA that is the test substance 90 is amplified. Thereby, under the control of the CPU 210, the turbidity in the detection cells 135 at the nucleic acid amplification reaction is generated in real time, based on the detection signal of the light receiving units 142.

In step S3, a first measured value 11 is acquired by the CPU 210. That is, the CPU 210 acquires the rise time of the turbidity from the turbidity change generated in step S2 until reaching the threshold (turbidity 0.1). The CPU 210 acquires the concentration of CK19 mRNA that is the test substance 90 as the first measured value 11, based on the rise time of the turbidity and the calibration curve (see FIG. 13) prepared in advance before the start of the measurement.

When the first measured value 11 is acquired, in step S4, the CPU 210 acquires arithmetic information 30 from a hard disk 223. Then, in step S5, the CPU 210 operates the first measured value 11 to an arithmetic value 22 by the arithmetic information 30. In step S6, the CPU 210 performs qualitative determination, based on the first measured value 11 and a first cut-off value 15, or based on the arithmetic value 22 and a second cut-off value 25.

In step S7, the CPU 210 displays the measurement result on the measurement result display screen 300. That is, a graph showing the temporal change of the turbidity of the biological sample, the amplification rise time, at least one of the first measured value 11 and the arithmetic value 22, and the determination result of the qualitative determination are displayed. Thereby, the measurement processing is completed.

EXAMPLES

Example 1

Hereinafter, by performing nucleic acid amplification by the LAMP method, using mRNA of cytokeratin 19 (CK19) as a test substance 90, an example of arithmetic information 30 for operating a first measured value 11 using a first measurement reagent 10 for measuring the concentration of CK19 mRNA to an arithmetic value 22 corresponding to a measured value of a second measurement reagent 20 will be shown.

(1.1 First Measurement Reagent and Second Measurement Reagent)

Figure 15:
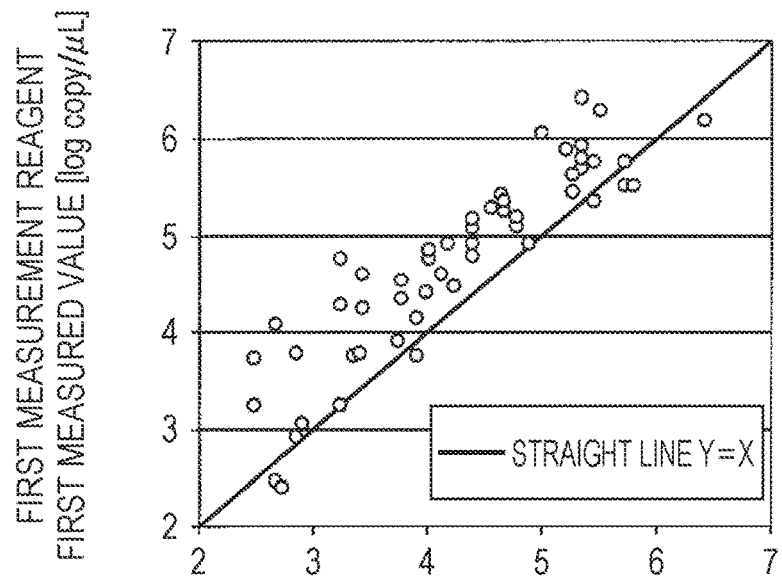
FIG. 15 is a correlation diagram between a first measured value and a second measured value for the same specimen according to Example 1.

The compositions of the first measurement reagent 10 and the second measurement reagent 20 are as shown in FIG. 9. FIG. 15 is a correlation diagram in which the measured value of the first measurement reagent 10 is taken on the Y axis as a first coordinate axis 41 and the measured value of the second measurement reagent 20 is taken on the X axis as a second coordinate axis 42, and the results of a correlation test in which measurement results for the common biological sample are plotted are shown. Measured values on each axis are shown as logarithmic values (log copy/μL). The cut-off values indicating the same qualitative determination by the first measurement reagent 10 and the second measurement reagent 20 are as shown in Table 1. In the present example, there are two pairs (+/−) and (++/+) of a first cut-off value 15 and a second cut-off value 25.

TABLE 1

First cut-off value and second cut-off value

| | | First measurement reagent First cut-off value (y) | | Second measurement reagent Second cut-off value (x) |
|---|---|---|---|---|
| +/− | y1 | 2.952[log copies/uL] (895.4[copies/uL]) | x1 | 2.390[log copies/uL] (245.5[copies/uL]) |
| ++/+ | y2 | 4.131[log copies/uL] (13520.7[copies/uL]) | x2 | 3.695[log copies/uL] (4954.5[copies/uL]) |

(1.2 Determination of Arithmetic Expression)

Figure 16:
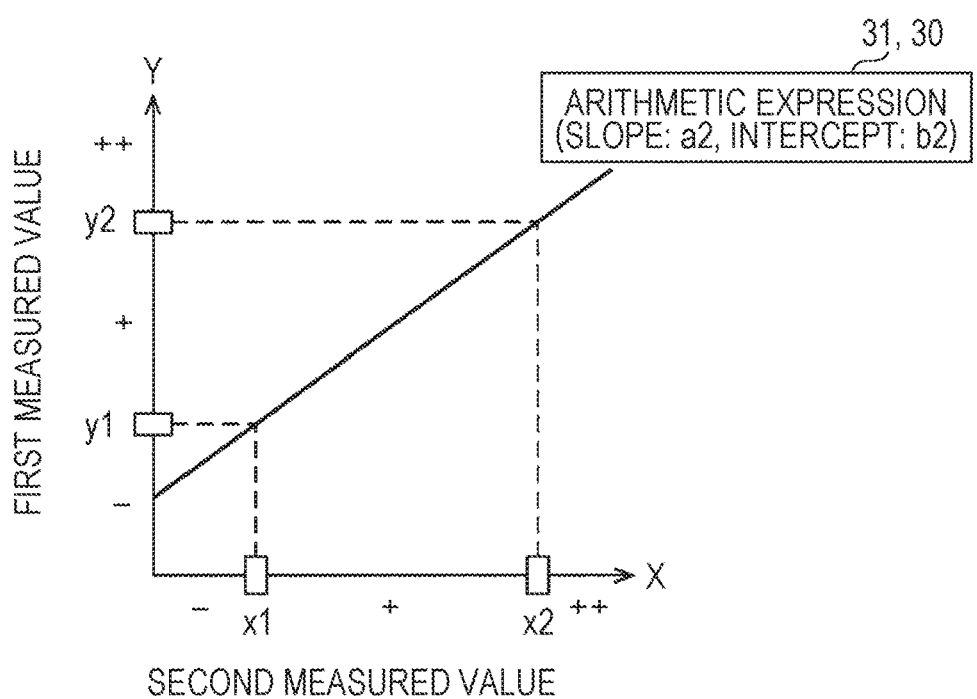
FIG. 16 is a diagram showing a method for obtaining an arithmetic expression according to Example 1.

From Table 1, the first cut-off values 15 of the first measurement reagent 10 shown in FIG. 16 are $y_1$=2.952 (Log copies/μL) and $y_2$=4.131 (Log copies/μL). The second cut-off values 25 of the second measurement reagent 20 are $x_1$=2.390 (Log copies/μL) and $x_2$=3.695 (Log copies/μL).

In the above formula (1), each cut-off value ($x_1$, $x_2$, $y_1$, $y_2$) was substituted into the slope $a_n=(y_n-y_{n-1})/(x_n-x_{n-1})$ and the intercept $b_n=y_{n-1}-(x_{n-1} \times a_n)$ to obtain the following values.
$a_2$=0.90345
$b_2$=0.79276

The obtained coefficient a2 and intercept b2 were substituted into the above formula (1) to obtain the following arithmetic expression 31.

$$Y' = (Y - b_n)/a_n \qquad (5)$$

$$= (Y - 0.79276)/0.90345$$

In the above formula (5), Y' is the arithmetic value 22 and Y is the first measured value 11.

Table 2 shows the qualitative determination results around the cut-off values before and after operation of the arithmetic expression 31 obtained as the above formula (5).

TABLE 2

Qualitative determination around cut-off values before and after operation

| | First measured value [log copies/uL] ([copies/uL]) | Arithmetic value [log copies/uL] ([copies/uL]) | Qualitative determination | |
|---|---|---|---|---|
| | | | First measured value | Arithmetic value |
| +/− | 2.950 (891.3) | 2.388 (244.3) | − | − |
| | 2.951 (893.3) | 2.389 (244.9) | − | − |
| | 2.952 (895.4) | 2.390 (245.5) | + | + |
| | 2.953 (897.4) | 2.391 (246.0) | + | + |
| ++/+ | 4.129 (13458.6) | 3.693 (4931.7) | + | + |
| | 4.13 (13489.6) | 3.694 (4943.1) | + | + |
| | 4.131 (13520.7) | 3.695 (4954.5) | ++ | ++ |
| | 4.132 (13551.9) | 3.696 (4965.9) | ++ | ++ |

As shown in Table 2, the qualitative determination results before and after operation matched, in both the (+/−) and (++/+) cut-off values. That is, when the qualitative determination result based on the first cut-off value 15 for the first measured value 11 before operation and the qualitative determination result based on the second cut-off value 25 for the arithmetic value 22 after operation matched with each other.

Example 2

The arithmetic expression 31 obtained in Example 1 above was adapted to the results of clinical trials, and it was confirmed that the arithmetic expression 31 can also be adapted to the case of clinical trials. In order to establish this confirmation method, standards were set, and the success or failure of retrospective analysis based on them was verified. Confirmation was made on the results of clinical trials of breast cancer, colorectal cancer and stomach cancer. The number of data N used for confirming the arithmetic expression is as follows. Breast cancer: N=300, colorectal cancer: N=149, stomach cancer: N=135

(2.1 Standards of Qualitative Performance of Arithmetic Expression)

<Standards 1 and 2: Consistency of Qualitative Determination Results Between First Measured Value and Second Measured Value>

The first measurement reagent 10 and the second measurement reagent 20 are considered to have equivalent clinical performance. Therefore, consistency of the qualitative determination results between a first measured value 11 and a second measured value 21 of the operation destination was confirmed as a premise of operation from the first measured value 11 to an arithmetic value 22. That is, a determination table shown in Table 3 was prepared, and whether or not there is a significant difference in the qualitative determination between the two groups of the qualitative determination result based on the first measured value 11 and the qualitative determination result based on the second measured value 21 was examined by McNemar's test. In Table 3, when b+c is 5 or less, the reliability of McNemar's test is lowered. Thus, a binomial test was used, and the result of no significant difference was used as acceptance criteria. Although not shown in Table 3, not only the determination of (++) and (+,-) but also two patterns of (+) and (-) determination were performed.

TABLE 3

Comparison of determination matching rates between first measured value and second measured value

|  |  | Second measured value | | |
| --- | --- | --- | --- | --- |
|  |  | Positive (++) | Negative (+, -) | |
| First measured value | Positive (++) | a | b | a + b |
|  | Negative (+, -) | c | d | c + d |
|  |  | a + c | b + d | N |

For calculation of the chi-square value in McNemar's test, the following formula (6) was used (yate's operation). The p value was calculated from the value calculated by the formula (6), and when the obtained p value was 0.05 or more (no significant difference), it was defined as pass (Standard 1).

[Expression 1]

$$\chi_0^2 = \frac{(|b-c|-1)^2}{b+c} \quad (6)$$

For the binomial test, the following formula (7) was used. The p value was calculated from this calculation formula, and when the obtained p value was 0.05 or more, it was defined as pass (Standard 2).

[Expression 2]

$$p(x) = 2 \times \sum_{l=0}^{min(b,c)} Nc_i \times \left(\frac{1}{2}\right)^N \quad (7)$$

<Standards 3 and 4: Consistency of Qualitative Determination Results Between Arithmetic Value and Second Measured Value>

The arithmetic value 22 and the second measured value 21 are considered to have equivalent clinical performance. Therefore, according to the determination table shown in Table 4, and whether or not there is a significant difference in the qualitative determination between the two groups of the qualitative determination result based on the arithmetic value 22 and the qualitative determination result based on the second measured value 21 was examined by McNemar's test. When b+c is 5 or less, a binomial test was used, and the result of no significant difference was used as acceptance criteria. Although not shown in Table 4, not only the determination of (++) and (+/-) but also two patterns of (++/+) and (-) determination were performed.

TABLE 4

Comparison of determination matching rates between arithmetic value and second measured value

|  |  | Second measured value | | |
| --- | --- | --- | --- | --- |
|  |  | Positive (++) | Negative (+, -) | |
| Arithmetic value | Positive (++) | a | b | a + b |
|  | Negative (+, -) | c | d | c + d |
|  |  | a + c | b + d | N |

For calculation of the chi-square value in McNemar's test, the p value was calculated from the value calculated using the formula (6), and when the obtained p value was 0.05 or more (no significant difference), it was defined as pass (Standard 3). For the binomial test, the p value was calculated using the above formula (7), and when the obtained p value was 0.05 or more, it was defined as pass (Standard 4).

<Standard 5: Consistency of Qualitative Determination Results of First Measured Value and Arithmetic Value>

According to the arithmetic expression 31 shown in the above formula (5), since a straight line passing through two points of the cut-off values is used, the qualitative determination based on the first measurement reagent 10 and the qualitative determination based on the arithmetic value 22 should be necessarily equal to each other. Therefore, based on the determination table shown in Table 5, the matching rate of determination was obtained, between two groups of the qualitative determination result based on the first measured value 11 and the first cut-off value 15 and the qualitative determination result based on the arithmetic value 22 and the second cut-off value 25. The determination matching rate of 100% was used as acceptance criteria (Standard 5).

TABLE 5

Comparison of determination matching rates between first measured value and arithmetic value

|  |  | First measured value | | |
| --- | --- | --- | --- | --- |
|  |  | Positive (++) | Negative (+, −) | |
| Arithmetic value | Positive (++) | a | b | a + b |
|  | Negative (+, −) | c | d | c + d |
|  |  | a + c | b + d | N |

In Table 5, the determination matching rate was defined as (a+d)/N (%).

<Standards 6 and 7: Slope in Consideration of Variation in Specimen Group>

Figure 17:
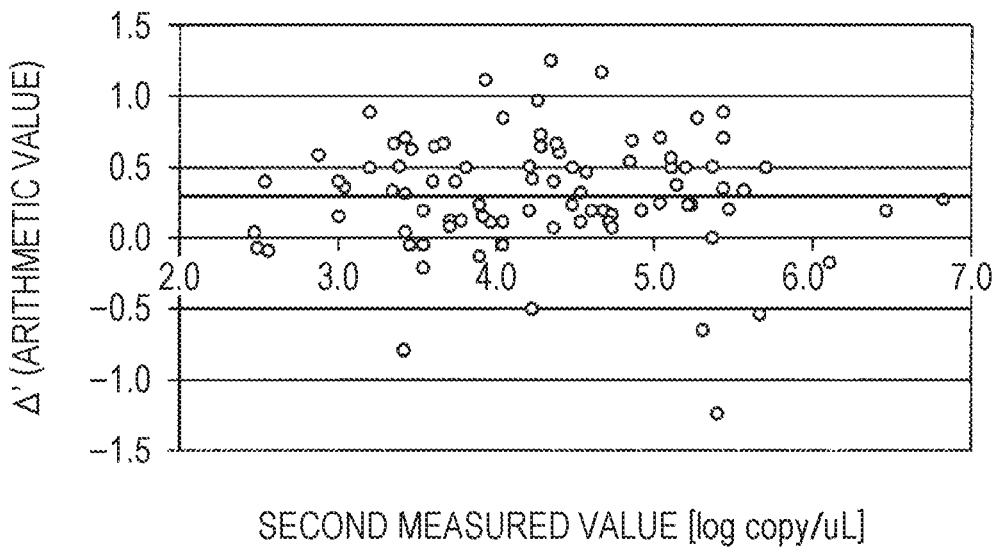
FIG. 17 is a plot of residuals of arithmetic values—second measured values for each specimen according to Example 2.
Figure 18:
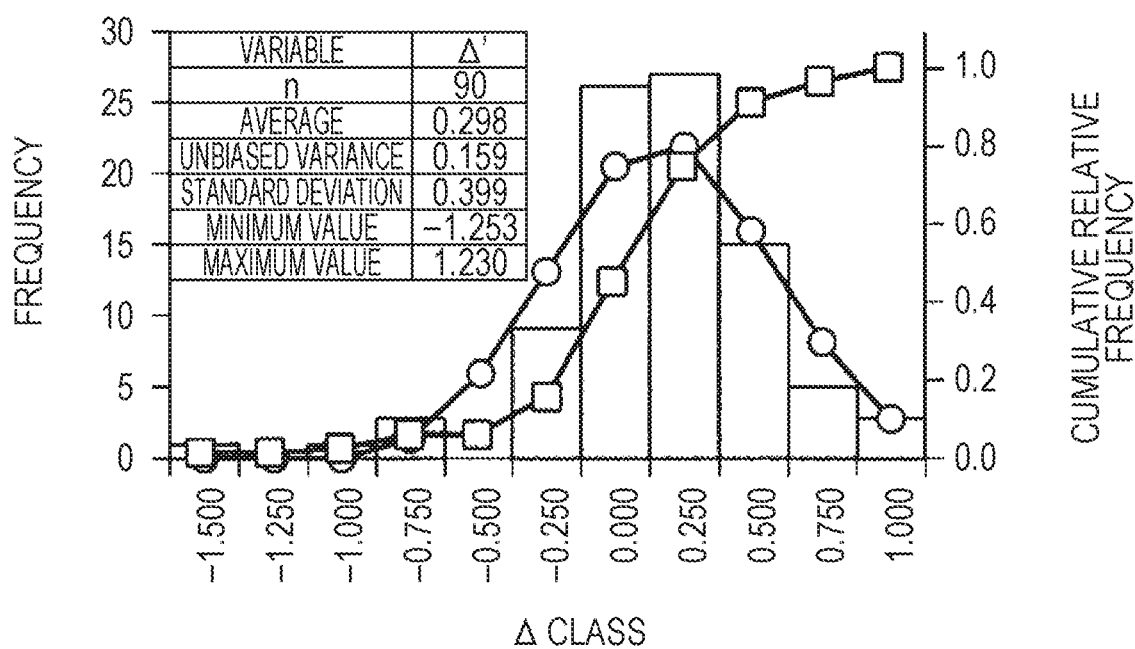
FIG. 18 is a frequency distribution of residuals of arithmetic values for each specimen shown in FIG. 17.

In the correlation diagram in which the arithmetic value 22 is plotted on the Y axis and the second measured value 21 is plotted on the X axis, the standard deviation from the straight line of Y=X is a variation in the specimen group, and when the regression line of the arithmetic value 22 and the second measured value 21 is prepared, the slope is considered to fall within the range of the standard deviation. In order to evaluate the degree of divergence from the straight line of Y=X of the plot of the arithmetic value 22 and the second measured value 21 with respect to the specimen group shown in FIG. 15, the plot of residuals Δ' of the arithmetic value 22 shown in FIG. 17 and the distribution table of residuals shown in FIG. 18 were prepared. The residual Δ' is the Y-axis direction distance of the plot from the straight line of Y=X (see FIG. 20). The standard deviation of the arched distribution in FIG. 18 represents the variation in the specimen group.

For the slope, the standard deviation was adopted as a parameter in order to take into consideration the variation in specimen group. In order to set the maximum value and minimum value of the slope of the regression line within the standard deviation, the range of the X axis is set. The range of the regression line was set as $X_{min}$=2.398, $X_{max}$=8.878 (7.398+20%), based on the range of the measured value by the second measurement reagent 20 (2.398 to 7.398 [log copy/μL]). The upper limit $Y_{max}$ ($X_{min}$) and the lower limit $Y_{min}$ ($X_{min}$) at the point $X_{min}$ and the upper limit $Y_{max}$ ($X_{max}$) and the lower limit $Y_{min}$ ($X_{max}$) at the point $X_{max}$ were obtained, taking the standard deviation into consideration at two points of $X_{min}$ and $X_{max}$.

Figure 19:
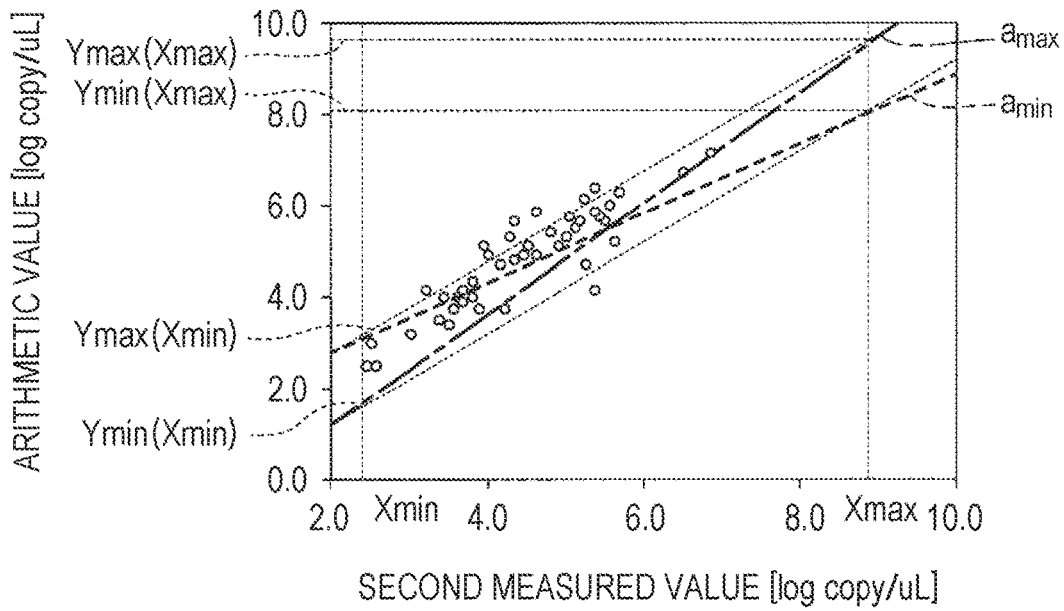
FIG. 19 is a diagram showing a slope range of a regression line based on FIGS. 16 and 17.

As shown in FIG. 19, according to the combination of the respective points of the upper limit and the lower limit, the slope of the regression line become the maximum value and the minimum value at a straight line (slope $a_{min}$) passing through two points ($X_{min}$, $Y_{max}$) and ($X_{max}$, $Y_{min}$), and a straight line (slope $a_{max}$) passing through two points ($X_{min}$, $Y_{min}$) and ($X_{max}$, $Y_{max}$), respectively. From this result, it was set as the standard that the following equations are satisfied by the slope a and the intercept b of the regression equation (y=ax+b) when the arithmetic value 22 is plotted on the Y axis and the second measured value 21 is plotted on the X axis.

0.75370 ≤ Slope $a$ of Regression Line ≤ 1.24630      (Standard 6)

−1.38862 ≤ Intercept $b$ of Regression Line ≤ 1.38862      (Standard 7)

<Standard 8: Equivalence Between Arithmetic Value 22 and Second Measured Value 21>

Figure 20:
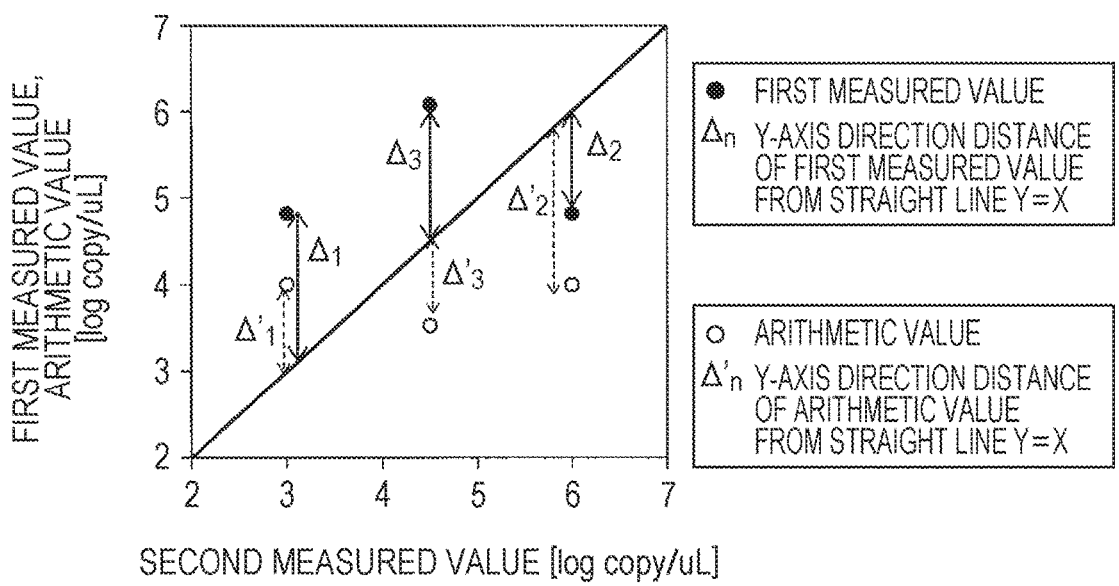
FIG. 20 is a schematic diagram for describing a distance from a straight line Y=X in a correlation diagram between a first measured value or an arithmetic value and a second measured value.

The arithmetic value 22 is considered to approach the second measured value 21 as compared with the first measured value 11. Therefore, the smaller the Y-axis direction distance from the straight line of Y=X of the plot in the correlation diagram between the second measured value 21 and the arithmetic value 22, as compared with the plot in the correlation diagram between the first measured value 11 and the second measured value 21, the more likely it is the equivalence. Therefore, as shown in FIG. 20, the distance in the Y-axis direction of each plot was defined as Δ, and it was set as Standard 8 that the following formula (8) is satisfied.

[Expression 3]

$$\sum_{i=1}^{N} |\Delta_i| \geq \sum_{i=1}^{N} |\Delta'_i| \quad (8)$$

wherein Δ is the Y-axis direction distance with respect to the straight line Y=X of the plot in the correlation diagram between the first measured value (Y axis) and the second measured value (X axis), and Δ' is the Y-axis direction distance with respect to the straight line Y=X of the plot in the correlation diagram between the arithmetic value (Y axis) and the second measured value (X axis)

(2.2 Validation Result of Each Standard)

It could be confirmed that all the standards were met, and operation was appropriate, in each data set of breast cancer (N=300), colorectal cancer (N=149), and stomach cancer (N=135). The validation results will be described for each data set hereinbelow.

<Results of Validation on Standards of Qualitative Performance for Breast Cancer Specimen>

Standard 1 to Standard 4

Table 6 shows determination results of the first measured value 11 and the arithmetic value 22 and the second measured value 21. According to Table 6, no significant difference was found in the McNemar's test and the binomial test (p value ≥ 0.05), and each of the measured values and the arithmetic values met Standards 1 to 4, respectively.

TABLE 6

Determination matching rates between first measured value (arithmetic value) and second measured value in breast cancer specimen

|  |  | Second measured value | | | | |
| --- | --- | --- | --- | --- | --- | --- |
|  |  | ++ | + | +I | − | |
| First measured value (Arithmetic value) | ++ | 63 | 4 | 3 | 0 | 70 |
|  | + | 3 | 25 | 5 | 6 | 39 |
|  | − | 0 | 7 | 1 | 183 | 191 |
|  |  | 66 | 36 | 9 | 189 | 300 |

| | |
| --- | --- |
| Positive negative matching rate | 95.3% |
| Matching rate other than ++/++ | 96.7% |
| Sensitivity | 92.8% |
| Specificity | 96.8% |
| PPV | 94.5% |
| NPV | 95.8% |
| McNemar_p value +/− (Standards 1, 3) | 0.789 |
| Binominal test_p value +/− (Standards 1, 3) | 1.157 |
| McNemar_p value ++/+, − (Standards 2, 4) | 0.343 |
| Binominal test_p value ++/+, − (Standards 2, 4) | 0.344 |

In Table 6, the determination result (+I) is a flag indicating that there is a possibility that amplification inhibition has occurred since the measurement results of the biological sample (negative) and the diluted sample (positive) do not match. PPV is positive predictive value, and NPV is negative predictive value.

Standard 5

Table 7 shows qualitative determination results based on the first measured value 11 and the first cut-off value 15 and qualitative determination results based on the arithmetic value 22 and the second cut-off value 25 in the breast cancer specimen. According to Table 7, the determination matching rate (=(a+d)/N (%)) was 100%, which met Standard 5.

TABLE 7

Determination matching rates before and after operation in breast cancer specimen

|  |  | First measured value | | | |
|---|---|---|---|---|---|
|  |  | ++ | + | − |  |
| Arithmetic | ++ | 70 | 0 | 0 | 70 |
| value | + | 0 | 39 | 0 | 39 |
|  | − | 0 | 0 | 191 | 191 |
|  |  | 70 | 39 | 191 | 300 |
| Positive negative matching rate |  |  | 100.0% | | |
| Matching rate other than ++/++ |  |  | 100.0% | | |
| Sensitivity |  |  | 100.0% | | |
| Specificity |  |  | 100.0% | | |
| PPV |  |  | 100.0% | | |
| NPV |  |  | 100.0% | | |

Standards 6 and 7

Figure 21:
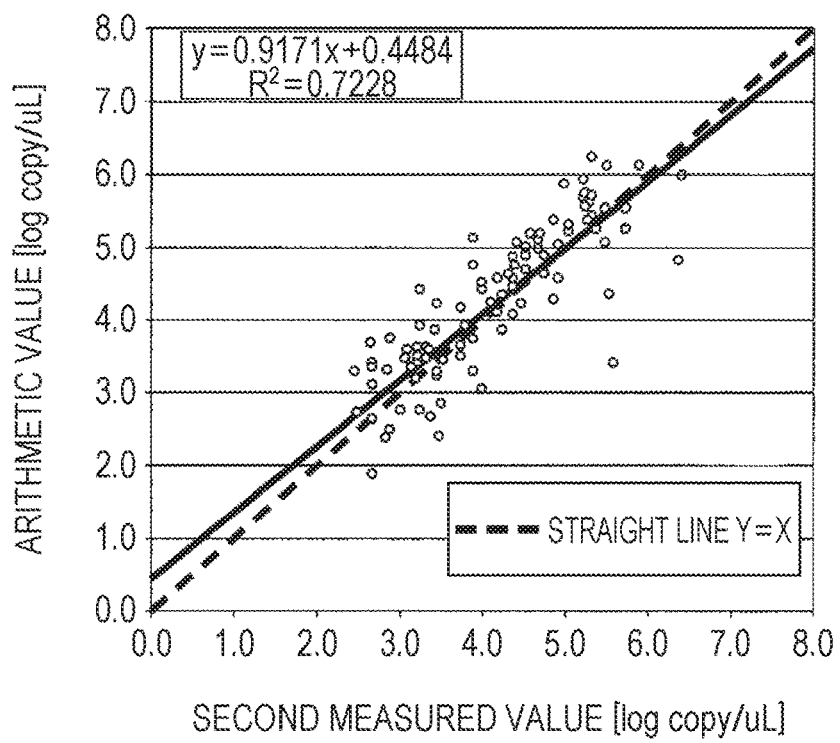
FIG. 21 is a diagram showing a regression line between a second measured value and an arithmetic value for a breast cancer specimen.

FIG. 21 shows a correlation diagram between the arithmetic value 22 (Y axis) and the second measured value 21 (X axis) in the breast cancer specimen and a regression line of the plot. The slope a of the regression line was 0.9171, which met Standard 6 (0.75370≤a≤1.24630). The intercept b of the regression line was 0.4484, which met Standard 7 (−1.38862≤b≤1.38862).

Standard 8

A correlation diagram between the first measured value (Y axis) and the second measured value (X axis) in the breast cancer specimen and a correlation diagram between the arithmetic value (Y axis) and the second measured value (X axis) in the breast cancer specimen were each prepared, and the Y-axis direction distances Δ and Δ' with respect to the straight line Y=X of each plot were acquired. The average value of Σ|Δ| was 0.58, and the average value of Σ|Δ'| was 0.44. Based on the above formula (8), Standard 8 was met.

<Results of Validation on Standards of Qualitative Performance for Colorectal Cancer Specimen>

Standard 1 to Standard 4

Table 8 shows determination results of the first measured value 11 and the arithmetic value 22 and the second measured value 21. According to Table 8, no significant difference was found in the McNemar's test and the binomial test (p value≥0.05), and each of the measured values and the arithmetic values met Standards 1 to 4, respectively,

TABLE 8

Determination matching rates between first measured value (arithmetic value) and second measured value in colorectal cancer specimen

|  |  | Second measured value | | | | |
|---|---|---|---|---|---|---|
|  |  | ++ | + | +I | − |  |
| First measured value | ++ | 39 | 2 | 3 | 0 | 44 |
| (Arithmetic value) | + | 3 | 5 | 0 | 3 | 11 |
|  | − | 0 | 3 | 0 | 91 | 94 |
|  |  | 42 | 10 | 3 | 94 | 149 |

TABLE 8-continued

Determination matching rates between first measured value (arithmetic value) and second measured value in colorectal cancer specimen

| Positive negative matching rate | 96.0% |
|---|---|
| Matching rate other than ++/++ | 94.6% |
| Sensitivity | 94.5% |
| Specificity | 96.8% |
| PPV | 94.5% |
| NPV | 96.8% |
| McNemar_p value +/− (Standards 1, 3) | 0.683 |
| Binominal test_p value +/− (Standards 1, 3) | 1.313 |
| McNemar_p value ++/+, − (Standards 2, 4) | 0.724 |
| Binominal test_p value ++/+, − (Standards 2, 4) | 0.727 |

Standard 5

Table 9 shows qualitative determination results based on the first measured value 11 and the first cut-off value 15 and qualitative determination results based on the arithmetic value 22 and the second cut-off value 25 in the colorectal cancer specimen. According to Table 9, the determination matching rate (=(a+d)/N (%)) was 100%, which met Standard 5.

TABLE 9

Determination matching rates before and after operation in colorectal cancer specimen

|  |  | First measured value | | | |
|---|---|---|---|---|---|
|  |  | ++ | + | − |  |
| Arithmetic | ++ | 44 | 0 | 0 | 44 |
| value | + | 0 | 11 | 0 | 11 |
|  | − | 0 | 0 | 94 | 94 |
|  |  | 44 | 11 | 94 | 149 |
| Positive negative matching rate |  |  | 100.0% | | |
| Matching rate other than ++/++ |  |  | 100.0% | | |
| Sensitivity |  |  | 100.0% | | |
| Specificity |  |  | 100.0% | | |
| PPV |  |  | 100.0% | | |
| NPV |  |  | 100.0% | | |

Standards 6 and 7

Figure 22:
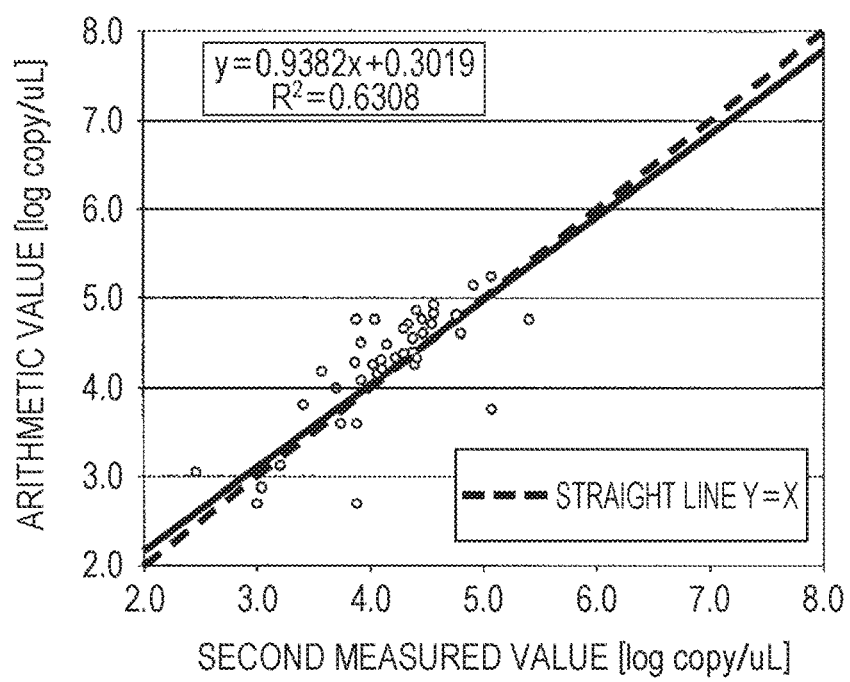
FIG. 22 is a diagram showing a regression line between a second measured value and an arithmetic value for a colorectal cancer specimen.

FIG. 22 shows a correlation diagram between the arithmetic value 22 (Y axis) and the second measured value 21 (X axis) in the colorectal cancer specimen and a regression line of the plot. The slope a of the regression line was 0.9382, which met Standard 6 (0.75370≤a≤1.24630). The intercept b of the regression line was 0.3019, which met Standard 7 (−1.38862≤b≤1.38862).

Standard 8

A correlation diagram between the first measured value (Y axis) and the second measured value (X axis) in the colorectal cancer specimen and a correlation diagram between the arithmetic value (Y axis) and the second measured value (X axis) in the colorectal cancer specimen were each prepared, and the Y-axis direction distances Δ and Δ' with respect to the straight line Y=X of each plot were acquired. The average value of Σ|Δ| was 0.52, and the average value of Σ|Δ'| was 0.28. Based on the above formula (8), Standard 8 was met.

<Results of Validation on Standards of Qualitative Performance for Stomach Cancer Specimen>

Standard 1 to Standard 4

Table 10 shows determination results of the first measured value 11 and the arithmetic value 22 and the second measured value 21. According to Table 10, no significant difference was found in the McNemar's test and the binomial test (p value≥0.05), and each of the measured values and the arithmetic values met Standards 1 to 4, respectively.

TABLE 10

Determination matching rates between first measured value (arithmetic value) and second measured value in stomach cancer specimen

| | | Second measured value | | | | |
|---|---|---|---|---|---|---|
| | | ++ | + | +I | − | |
| First measured value | ++ | 32 | 0 | 0 | 0 | 32 |
| (Arithmetic value) | + | 2 | 9 | 0 | 0 | 11 |
| | − | 0 | 0 | 1 | 91 | 92 |
| | | 34 | 9 | 1 | 91 | 135 |

| | |
|---|---|
| Positive negative matching rate | 99.3% |
| Matching rate other than ++/++ | 98.5% |
| Sensitivity | 97.7% |
| Specificity | 100.0% |
| PPV | 100.0% |
| NPV | 98.9% |
| McNemar_p value +/− (Standards 1, 3) | 1.000 |
| Binominal test_p value +/− (Standards 1, 3) | 1.000 |
| McNemar_p value ++/+, − (Standards 2, 4) | 0.4795 |
| Binominal test_p value ++/+, − (Standards 2, 4) | 0.500 |

Standard 5

Table 11 shows qualitative determination results based on the first measured value 11 and the first cut-off value 15 and qualitative determination results based on the arithmetic value 22 and the second cut-off value 25 in the stomach cancer specimen. According to Table 11, the determination matching rate (=(a+d)/N (%)) was 100%, which met Standard 5.

TABLE 11

Determination matching rates before and after operation in stomach cancer specimen

| | | First measured value | | | |
|---|---|---|---|---|---|
| | | ++ | + | − | |
| Arithmetic | ++ | 32 | 0 | 0 | 32 |
| value | + | 0 | 11 | 0 | 11 |
| | − | 0 | 0 | 92 | 92 |
| | | 32 | 11 | 92 | 135 |

TABLE 11-continued

Determination matching rates before and after operation in stomach cancer specimen

| | |
|---|---|
| Positive negative matching rate | 100.0% |
| Matching rate other than ++/++ | 100.0% |
| Sensitivity | 100.0% |
| Specificity | 100.0% |
| PPV | 100.0% |
| NPV | 100.0% |

Standards 6 and 7

Figure 23:
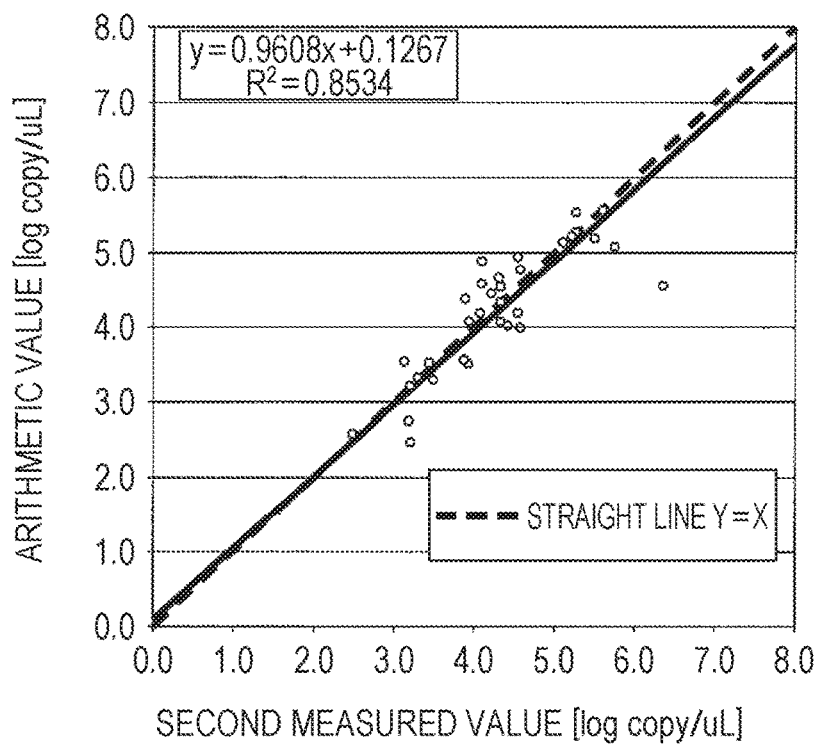
FIG. 23 is a diagram showing a regression line between a second measured value and an arithmetic value for a stomach cancer specimen.

FIG. 23 shows a correlation diagram between the arithmetic value 22 (Y axis) and the second measured value 21 (X axis) in the stomach cancer specimen and a regression line of the plot. The slope a of the regression line was 0.9608, which met Standard 6 (0.75370≤a≤1.24630). The intercept b of the regression line was 0.1267, which met Standard 7 (−1.38862≤b≤1.38862).

Standard 8

A correlation diagram between the first measured value (Y axis) and the second measured value (X axis) in the colorectal cancer specimen and a correlation diagram between the arithmetic value (Y axis) and the second measured value (X axis) in the colorectal cancer specimen were each prepared, and the Y-axis direction distances Δ and Δ' with respect to the straight line Y=X of each plot were acquired. The average value of Σ|Δ| was 0.39, and the average value of Σ|Δ'| was 0.23. Based on the above formula (8), Standard 8 was met.

Example 3

In order to confirm that the setting of the above arithmetic expression 31 is also effective for cases having three or more cut-off values, an arithmetic expression 31 with three cut-off values was acquired to confirm that the qualitative determination does not change before and after operation.

In Example 3, in addition to the two cut-off values (+/−) and (++/+) in Example 1, a third (+++/++) cut-off value was newly set. The cut-off values indicating the same qualitative determination between the first measurement reagent 10 and the second measurement reagent 20 are as shown in Table 12. In Table 12, values with dot after measured values are respective cut-off values.

TABLE 12

Cut-off values at three points

| | | | Qualitative determination | |
|---|---|---|---|---|
| | First measured value [log copies/uL] ([copies/uL]) | Second measured value [log copies/uL] ([copies/uL]) | First measured value | Second measured value |
| +/− | 2.950 (891.3) | 2.388 (244.3) | − | − |
| | 2.951 (893.3) | 2.389 (244.9) | − | − |
| | 2.952 (895.4) ● | 2.390 (245.5) ● | + | + |
| | 2.953 (897.4) | 2.391 (246.0) | + | + |
| ++/+ | 4.129 (13458.6) | 3.693 (4931.7) | + | + |
| | 4.13 (13489.6) | 3.694 (4943.1) | + | + |
| | 4.131 (13520.7) ● | 3.695 (4954.5) ● | ++ | ++ |
| | 4.132 (13551.9) | 3.696 (4965.9) | ++ | ++ |
| +++/++ | 5.37 (234422.9) | 4.693 (49317.3) | ++ | ++ |
| | 5.371 (234963.3) | 4.694 (49431.0) | ++ | ++ |
| | 5.372 (235504.9) ● | 4.695 (49545.0) ● | +++ | +++ |
| | 5.373 (236047.8) | 4.696 (49659.2) | +++ | +++ |

●: Cut-off value (3.1 Determination of Arithmetic Expression)

Figure 24:
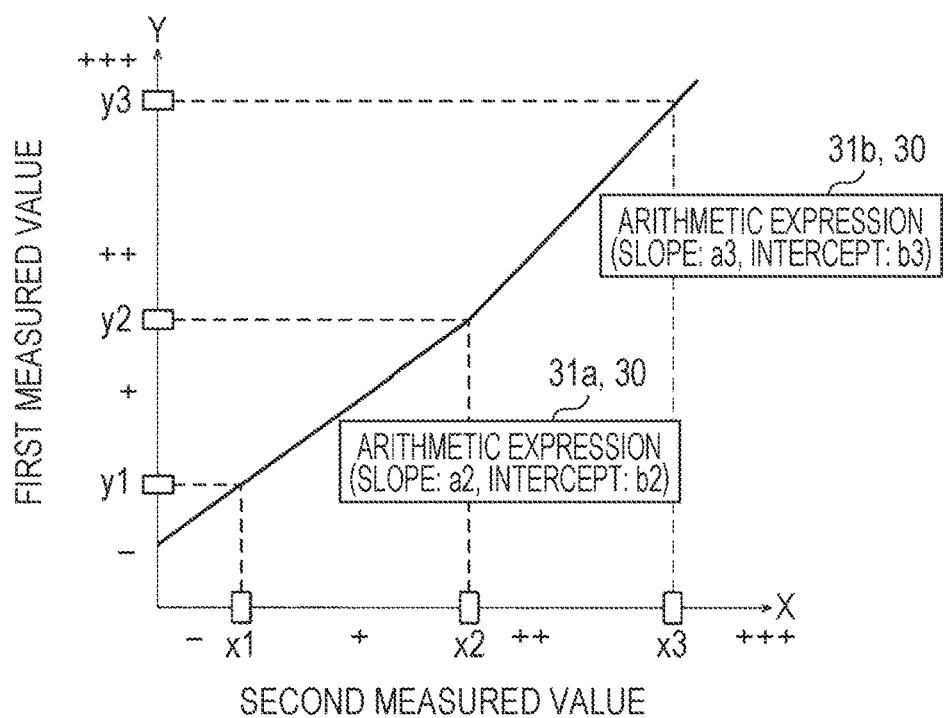
FIG. 24 is a diagram showing a method for obtaining an arithmetic expression by Example 3.

From Table 12, the first cut-off values 15 of the first measurement reagent 10 shown in FIG. 24 are $y_1=2.952$ (Log copies/μL), $y_2=4.131$ (Log copies/μL), $y_3=5.372$ (Log copies/μL). The second cut-off values 25 of the second measurement reagent 20 are $x_1=2.390$ (Log copies/μL), $x_2=3.695$ (Log copies/μL), $x_3=4.695$ (Log copies/μL).

In Example 3, the first arithmetic expression 31$a$ in the (+) section having two points of the (+/−) cut-off value ($x_1$, $y_1$) and the (++/+) cut-off value ($x_2$, $y_2$) as both ends, and the second arithmetic expression 31$b$ in the (++) section having two points of the (++/+) cut-off value ($x_2$, $y_z$) and the (+++/++) cut-off value ($x_3$, $y_3$) as both ends were acquired for each section.

<First Arithmetic Expression>

In the above formula (1), each cut-off value ($x_1$, $x_2$, $y_1$, $y_2$) was substituted into the slope $a_n=(y_n-y_{n-1})/(x_n-x_{n-1})$ and the intercept $b_n=y_{n-1}-(x_{n-1}\times a_n)$ to obtain the following values.

$a_2=0.90345$
$b_2=0.79276$

The obtained coefficient a2 and intercept b2 were substituted into the above formula (1) to obtain the following first arithmetic expression 31$a$.

$$Y' = (Y - b_n)/a_n \quad (9)$$
$$= (Y - 0.79276)/0.90345$$

The first arithmetic expression 31$a$ shown in the formula (9) is the same as the arithmetic expression (5) of Example 1.

<Second Arithmetic Expression>

In the above formula (1), each cut-off value ($x_2$, $x_3$, $y_2$, $y_3$) was substituted into the slope $a_n=(y_n-y_{n-1})/(x_n-x_{n-1})$ and the intercept $b_n=y_{n-1}-(x_{n-1}\times a_n)$ to obtain the following values.

$a_3=1.24100$
$b_3=-0.45449$

The obtained coefficient a3 and intercept b3 were substituted into the above formula (1) to obtain the following second arithmetic expression 31$b$.

$$Y' = (Y - b_n)/a_n \quad (10)$$
$$= (Y - (-0.45449))/1.24100$$

Thus, the arithmetic expression was defined as follows.
(1) A first measured value of (++/+) or less $$Y'=(Y-0.79276)/0.90345 \quad (9)$$

(2) A first measured value of larger than (++/+)

$$Y'=(Y-(-0.45449))/1.24100 \quad (10)$$

That is, the first arithmetic expression 31$a$ is applied in the (+) and (−) sections that are (++/+) or less, and the second arithmetic expression 31$b$ is applied in the (++) and (+++) sections that are larger than (++/+).

(3.2 Consistency of Qualitative Determination Results)

A qualitative determination result based on the first measured value 11 and the first cut-off value 15 and a qualitative determination result based on the arithmetic value 22 and the second cut-off value 25 were acquired using the obtained arithmetic expression. The qualitative determination results are shown in Table 13.

TABLE 13

Determination matching rates between arithmetic value and first measured value

| | | First measured value | | | | |
|---|---|---|---|---|---|---|
| | | +++ | ++ | + | − | |
| Arithmetic value | +++ | 88 | 0 | 0 | 0 | 88 |
| | ++ | 0 | 230 | 0 | 0 | 230 |
| | + | 0 | 0 | 105 | 0 | 105 |
| | − | 0 | 0 | 0 | 842 | 842 |
| | | 88 | 230 | 105 | 842 | 1265 |

As shown in Table 13, the qualitative determination results before and after operation matched, in any determination of (+++), (++), (+) and (−). That is, when the qualitative determination result based on the first cut-off value 15 for the first measured value 11 before operation and the qualitative determination result based on the second cut-off value 25 for the arithmetic value 22 after operation matched with each other. From this fact, it was shown that, by setting two or more cut-off values, the arithmetic information 30 of this embodiment can operate the first measured value 11 to the arithmetic value 22 corresponding to the second measured value 21, without affecting the qualitative determination.

Comparative Example

Hereinafter, in order to confirm the effect of the arithmetic information 30 of this embodiment, a comparative example in the case where the operation is executed by the arithmetic expression of the regression line prepared without being based on the cut-off value will be shown.

<Creation of Arithmetic Expression by Comparative Example>

In the comparative example, a regression line was obtained from the result of the correlation test between the first measured value 11 and the second measured value 21, and an arithmetic expression was created. The number of data N used for creating the arithmetic expression is 1265.

Figure 25:
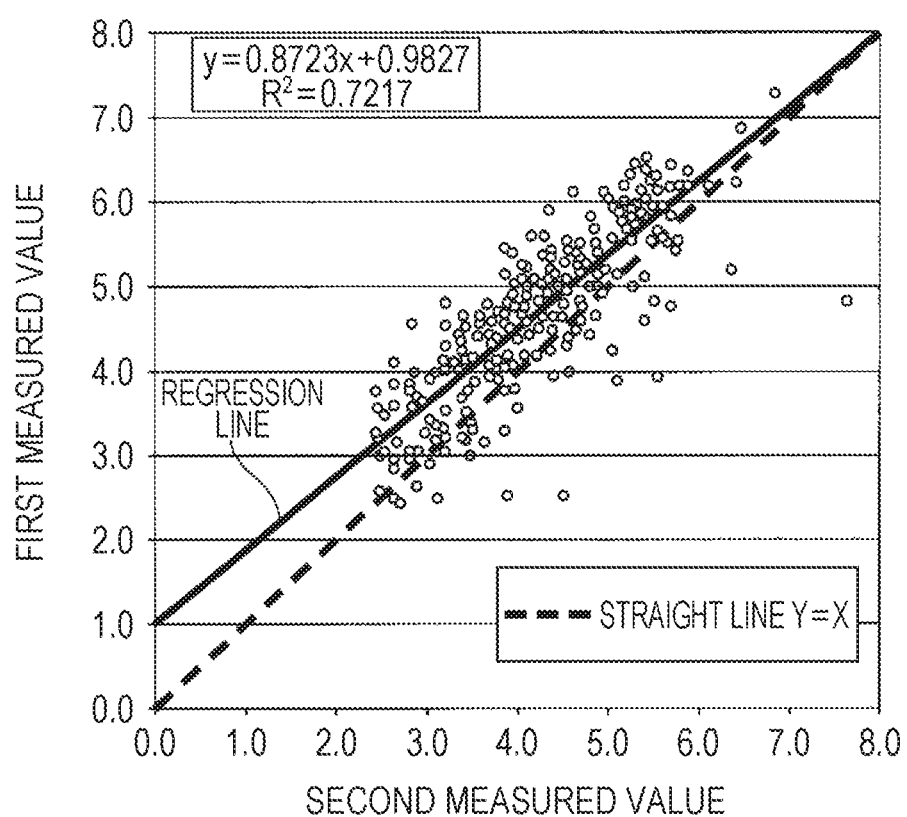
FIG. 25 is a correlation diagram between a first measured value and a second measured value by a comparative example.

FIG. 25 shows the results of the correlation test in which the measured value of the first measurement reagent 10 is taken on the Y axis and the measured value of the second measurement reagent 20 is taken on the X axis, and the measurement results for the common biological sample are plotted. The function of the regression line obtained from FIG. 25 was used as the arithmetic expression of the comparative example.

The arithmetic expression of the comparative example was represented by the following formula (11).

Comparative Example $$Y'=(Y-(0.9827))/0.8723 \quad (11)$$

<Consistency of Qualitative Determination Results in Comparative Example>

A qualitative determination result based on the first measured value 11 and the first cut-off value 15 and a qualitative determination result based on the arithmetic value using the arithmetic expression (11) by the comparative example and the second cut-off value 25 were acquired. The qualitative determination results are shown in Table 14.

TABLE 14

(Comparative Example) Comparison of arithmetic value and first measured value by regression equation

|  |  | First measured value | | | |
|---|---|---|---|---|---|
|  |  | ++ | + | − | |
| Arithmetic value by regression equation | ++ | 305 | 0 | 0 | 305 |
|  | + | 13 | 92 | 0 | 105 |
|  | − | 0 | 13 | 842 | 855 |
|  |  | 318 | 105 | 842 | 1265 |

As shown in Table 14, among 318 specimens determined to be (++) for the first measured value 11 before operation, 13 specimens determined to be (+) with respect to the arithmetic value using the arithmetic expression by the comparative example were generated. Among 105 specimens determined to be (+) for the first measured value 11 before operation, 13 specimens determined to be (−) with respect to the arithmetic value using the arithmetic expression by the comparative example were generated. For these specimens, it was confirmed that the qualitative determination result changes before and after operation using the arithmetic expression by the comparative example.

Other Embodiment

Figure 26:
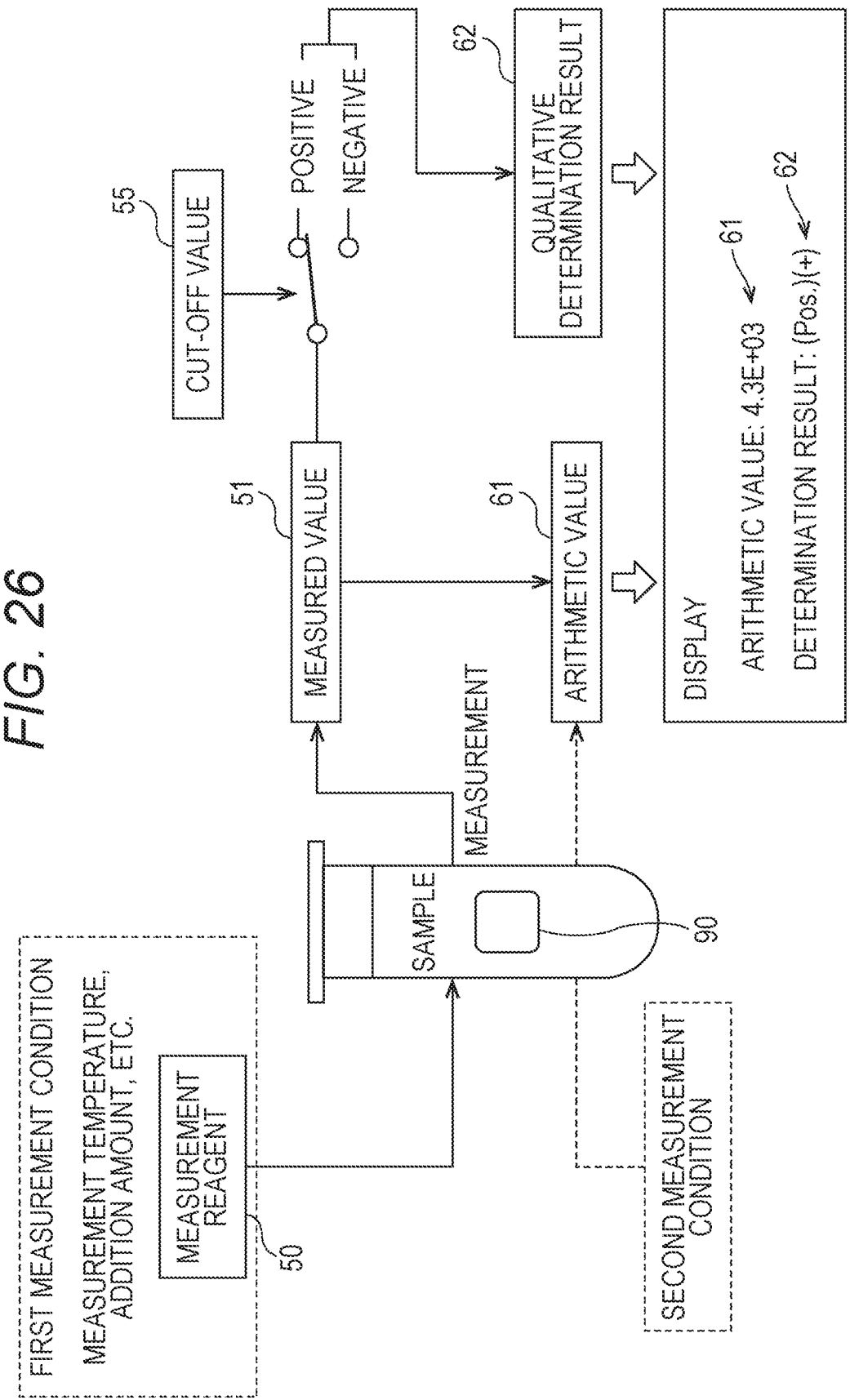
FIG. 26 is a diagram for describing an outline of a method for displaying a qualitative determination result.

FIG. 26 is a diagram showing a method for displaying a qualitative determination result according to other embodiment. With reference to FIG. 26, the outline of a method for displaying a qualitative determination result according to other embodiment will be described.

In the method for displaying a qualitative determination result, a measured value 51 of a test substance 90 is acquired under a first measurement condition, qualitative determination is performed on a specimen containing the test substance 90 by comparing the measured value 51 with a cut-off value 55, an arithmetic value 61 operated so as to correspond to a measured value when the measured value 51 is measured under a second measurement condition is obtained, and the arithmetic value 61 and a qualitative determination result 62 are displayed.

The measured value 51 is a measured value obtained by measurement under the first measurement condition. The measurement condition is a condition set for acquiring a measured value such as the type or composition of the measurement reagent 50 to be used, the temperature condition, the amount and concentration of the specimen, the addition amount of the measurement reagent 50, and the like. The measurement condition may be paraphrased as a measurement protocol. The examples shown in FIGS. 1 to 25 can be said as the case where the measurement reagent to be used is different among the measurement conditions. In the example of FIG. 26, any conditions, not limited to the measurement reagent, may be different between the first measurement condition and the second measurement condition. Therefore, the first measurement condition and the second measurement condition may be the same for the measurement reagent 50 to be used, and the measurement conditions other than the measurement reagent may be different. For example, a temperature condition may be different. The temperature condition may be different for each treatment step. The temperature condition may include each of temperature setting values of the temperature at the time of adding the measurement reagent 50 to the sample, the reaction temperature for causing the reaction after adding the measurement reagent 50, the temperature at the time of measurement after the reaction, and the like. Here, as in the example described above, the case where the measurement reagent to be used is different will be described.

The measurement reagent 50 is a reagent used for measuring the test substance 90 contained in the biological sample based on a predetermined measurement principle. The measurement reagent 50 generates chemical reactions with the test substance 90 or a substance associated with the test substance 90, so that the test substance 90 can be directly, or indirectly via other associated substances. By the measurement based on the predetermined measurement principle, the measured value 51 related to the test substance 90 is acquired.

The arithmetic value 61 is a value operated so as to correspond to the measured value when the measured value 51 obtained under the first measurement condition is measured under another second measurement condition. The operation method is not particularly limited. To obtain the arithmetic value 61, an arithmetic expression may be used, or an arithmetic table may be used. Even when the same specimen containing the test substance 90 is measured under the first measurement condition and the second measurement condition, respectively, the obtained measured values are different depending on the difference in the measurement conditions. Therefore, the first measurement condition and the second measurement condition are also different from each other in the cut-off value for performing the qualitative determination, and the cut-off value 55 for the measured value 51 under the first measurement condition and the cut-off value for the measured value under the second measurement condition can be set, respectively. In the example of FIG. 26, based on the measured value 51 of the test substance 90 obtained under the first measurement condition and the cut-off value 55 for the measured value obtained under the first measurement condition, the qualitative determination result 62 on the specimen including the test substance 90 is acquired. Therefore, the arithmetic value 61 is not needed to be used for the qualitative determination, and can be calculated irrespective of the cut-off value 55.

The qualitative determination result 62 obtained by using the measured value 51 before operation and the arithmetic value 61 after operation are both displayed. The display can be performed using a monitor, a projector or other display device. In this way, in the example of FIG. 26, the arithmetic value 61 to be displayed and the value (measured value 51) that is the basis of the qualitative determination result 62 to be displayed are different. The measured value 51 may be displayed together with the arithmetic value 61.

In the example of FIG. 26, in the case of using the arithmetic expression for obtaining the arithmetic value 61, the arithmetic expression may be a regression equation set irrespective of the cut-off value 55, as shown in the comparative example of FIG. 25. In FIG. 25, when qualitative determination was performed using the arithmetic expression by the comparative example and the second cut-off value 25, a discrepancy of the qualitative determination results between the first measured value 11 before operation and the first cut-off value 15 occurred (see Table 14). However, in the example of FIG. 26, the results of the measured value 51 before operation and the cut-off value 55 are used as the qualitative determination result 62 even after operation, thus the qualitative determination result 62 does not change before and after operation.

As described above, in the method for displaying a qualitative determination result of FIG. 26, according to the above configuration, even when displaying the arithmetic value 61 obtained by operating the measured value 51, it is possible to make a determination using the measured value 51 before operation for qualitative determination, and to display the qualitative determination result based on the measured value 51 before operation, and the arithmetic value 61 after operation. That is, even when displaying the arithmetic value 61 corresponding to the measured value in the case of using another second measurement condition different from the first measurement condition used for acquiring the measured value 51, the qualitative determination results using the measured value 51 before operation actually measured and the cut-off value 55 of the measurement reagent 50 used for the measurement are consistently displayed, instead of performing qualitative determination using the obtained arithmetic value 61 and the cut-off value of another second measurement condition, so that consistent qualitative determination results can be displayed before and after operation. As a result, it is possible to suppress change in clinical judgment before and after operation, when operating the measured value 51 obtained using a certain first measurement condition to the value in the case of using another second measurement condition in clinical examination.

Figure 27:
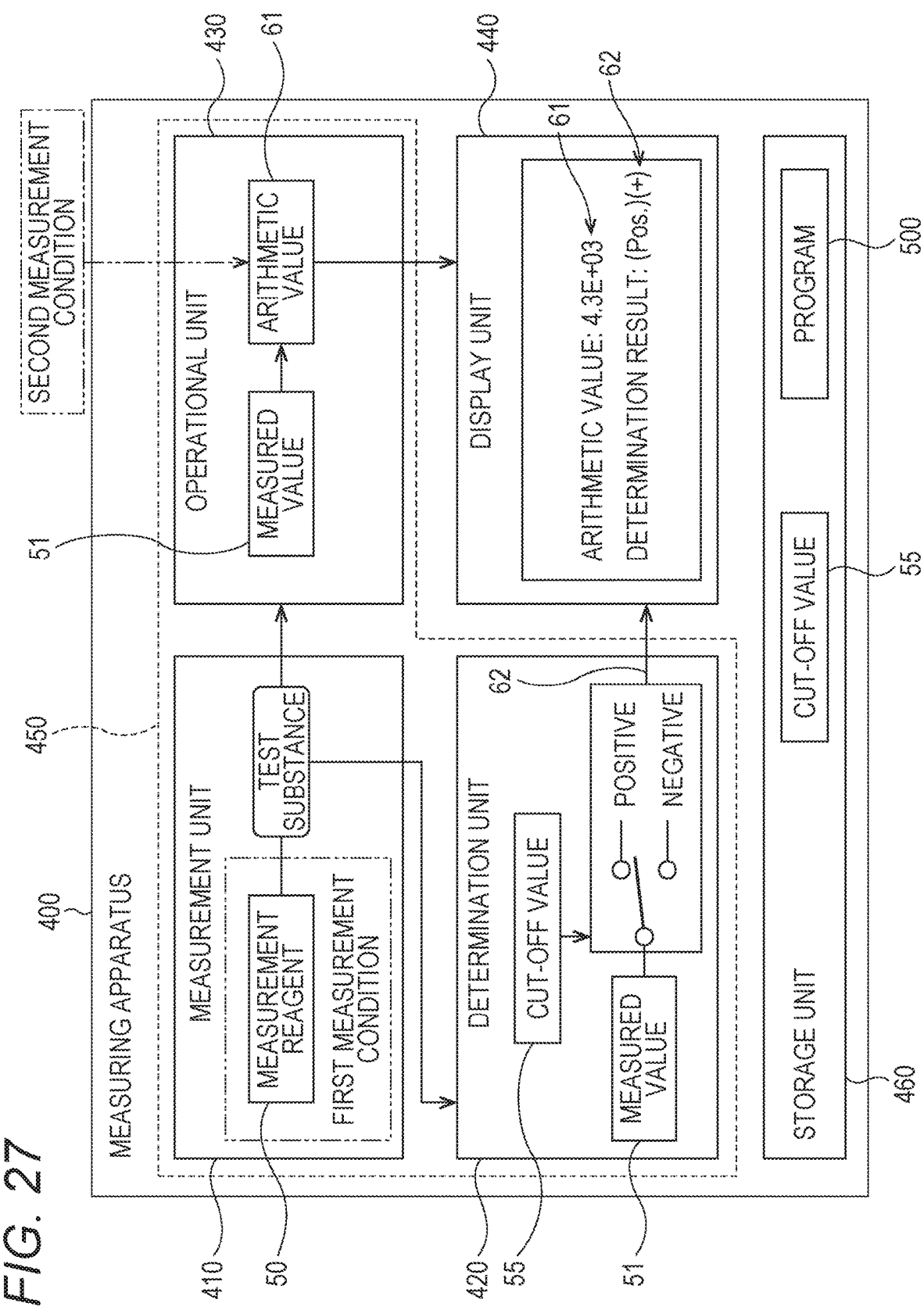
FIG. 27 is a diagram for describing a measuring apparatus that implements a method for displaying a qualitative determination result.
Figure 28:
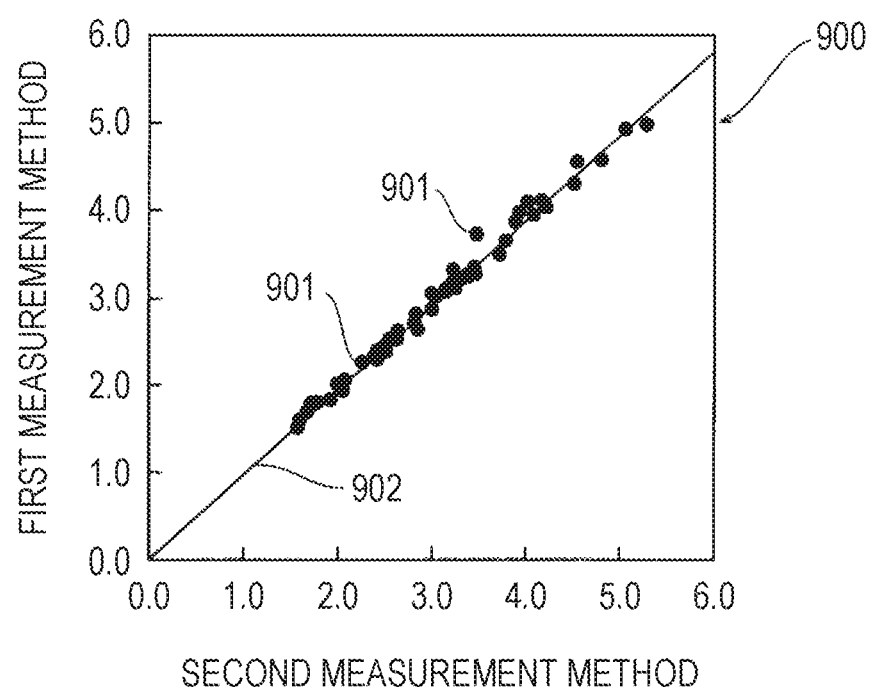
FIG. 28 is a diagram for describing an operation method of a first measured value by conventional art.

FIG. 27 shows an example of the measuring apparatus 400 that implements a method for displaying a qualitative determination result shown in FIG. 26.

The measuring apparatus 400 shown in FIG. 27 includes a measurement unit 410 for acquiring a measured value 51 of a test substance 90 under a first measurement condition, a determination unit 420 for performing qualitative determination on a specimen containing the test substance 90 by comparing the measured value 51 with a cut-off value 55, an operational unit 430 for obtaining an arithmetic value 61 operated so as to correspond to a measured value when the measured value 51 is measured under a second measurement condition, and a display unit 440 for displaying the arithmetic value 61 and a qualitative determination result 62. As the apparatus configuration of the measuring apparatus 400, the configuration similar to those shown in FIGS. 7 to 14 can be adopted. The configuration example of FIG. 27 differs from the examples shown in FIGS. 7 to 14 in that the acquisition of the arithmetic value 61 is not limited to the case of using the arithmetic information 30 (arithmetic expression 31) and may be an acquisition method using the regression equation like the comparative example shown in FIG. 25.

The measurement unit 410 has a function of reacting the measurement reagent 50 with, for example, a test substance 90 or a substance associated with the test substance 90. The measurement unit 410 has a function of directly or indirectly measuring the test substance 90, accompanying the test substance 90 or the substance associated with the test substance 90 and the chemical reaction. By measurement based on a predetermined measurement principle, the measurement unit 410 acquires a measured value relating to the test substance 90.

The measurement unit 410 can adopt the same configuration as the measurement unit 110. The measurement unit 410 may include a reaction section 130 and a turbidity detection section 140. The measurement unit 410 may include a tip placement section 150, a liquid container placement section 160, a dispensing section 170, and a tip disposal section 180 as shown in FIG. 8. Among the measurements performed by the measurement unit 410, processing related to acquisition of the amplification rise time and acquisition of the measured value 51 using the calibration curve can be performed by a computer including a CPU 450 and a storage unit 460.

The determination unit 420 compares the measured value 51 obtained under the first measurement condition by the measurement unit 410 with the cut-off value 55 for the measurement result obtained under the first measurement condition to perform qualitative determination on a specimen containing the test substance 90. The determination unit 420 compares the measured value 51 with the cut-off value 55. The determination unit 420 determines as positive when the measured value 51 is not less than the cut-off value 55, and determines as negative when the measured value 51 is less than the cut-off value 55. The determination unit 420 performs qualitative determination, based on the measured value 51 and the cut-off value 55, irrespective of the arithmetic value 61. The determination unit 420 can be configured by the computer including the CPU 450 and the storage unit 460.

The operational unit 430 operates the measured value 51 under the first measurement condition obtained by the measurement unit 410 according to a predetermined operation method, to obtain the arithmetic value 61 operated so as to correspond to the measured value when measured under another second measurement condition. As described above, for operation, an arithmetic expression may be used, or an arithmetic table may be used. The operation may use the arithmetic information 30 or the arithmetic expression 31. The arithmetic value 61 is not needed to be used for the qualitative determination, and can be calculated irrespective of the cut-off value 55. The operational unit 430 can be configured by the computer including the CPU 450 and the storage unit 460.

The display unit 440 displays the arithmetic value 61 obtained by the operational unit 430 and the qualitative determination result 62 acquired by the determination unit 420. In the example of FIG. 27, the arithmetic value 61 to be displayed and the value (measured value 51) that is the basis of the qualitative determination result 62 to be displayed are different. The display unit 440 may display the measured value 51 together with the arithmetic value 61. Also in the examples of FIGS. 26 and 27, as the display modes of the arithmetic value 61 and the qualitative determination result 62, it may be displayed like the measurement result display screen 300 shown in FIG. 11 or the measurement result display screen 350 shown in FIG. 12, or another display screen may be displayed. For example, in the case of the measurement result display screen 350 shown in FIG. 12, the qualitative determination result 62 is displayed in the determination result display column 371, and at least the arithmetic value 61 is displayed in the measured value display column 372.

In the measuring apparatus 400 according to the configuration example of FIG. 27, according to the above configuration, even when displaying the arithmetic value 61 obtained by operating the measured value 51, it is possible to make a determination using the measured value 51 before operation for qualitative determination, and to display the qualitative determination result 62 based on the measured value 51 before operation, and the arithmetic value 61 after operation. That is, even when displaying the arithmetic value 61 corresponding to the measured value in the case of using another second measurement condition different from the first measurement condition used for acquiring the measured value 51, the qualitative determination results using the measured value 51 before operation actually measured and the cut-off value 55 of the first measurement condition used for the measurement are consistently displayed, instead of performing qualitative determination using the obtained arithmetic value 61 and the cut-off value of another second measurement condition, so that consistent qualitative determination results can be displayed before and after operation. As a result, it is possible to suppress change in clinical judgment before and after operation, when operating the measured value 51 obtained using a certain first measurement condition to the value in the case of using another second measurement condition in clinical examination.

In the examples of FIGS. 26 and 27, the arithmetic value 61 is a value corresponding to a measured value when measured using another measurement reagent (not shown) that acts under the same measurement principle as the measurement reagent 50. For example, the measurement reagent 50 used in the first measurement condition is the first measurement reagent 10, and the measurement reagent used in another second measurement condition is the second measurement reagent 20. Thereby, since the measurement reagent 50 used for the measurement under the first measurement condition and another measurement reagent for obtaining the measured value under the second measurement condition to be operated are reagents acting on the same measurement principle, not a reagent acting on a completely different measurement principle, high correlation is recognized also between the measured values, thus operation can be performed with high accuracy. In the examples shown in FIG. 26 and FIG. 27, it may also be operated to the measured value when measured using another measurement reagent that acts under the measurement principle different from the measurement reagent 50.

In the examples of FIGS. 26 and 27, the measurement reagent 50 and another measurement reagent corresponding to the arithmetic value 61 act on the same measurement principle and have compositions different from each other. For example, the measurement reagent 50 is the first measurement reagent 10 shown in FIG. 9, and the other measurement reagent is the second measurement reagent 20 shown in FIG. 9. Thereby, since it is basically the same kind of reagents acting on the same measurement principle, high correlation is recognized also between the measured values, thus operation can be performed with higher accuracy.

In the examples of FIGS. 26 and 27, the cut-off value 55 is a threshold for performing qualitative determination on at least one of a biological sample containing the test substance 90 and a specimen containing the biological sample. This makes it possible to operate the measured value 51 without changing the qualitative determination such as positive or negative for the examination item before and after operation in clinical examination. On the other hand, in addition to the qualitative determination result 62, as for the arithmetic value 61 of the measured value 51 measured using the first measurement condition, it can be compared with a data measured using another second measurement condition in the past, and statistically handled along with the data measured using another second measurement condition.

In the examples of FIGS. 26 and 27, the qualitative determination result 62 indicates the presence or absence of suspected disease or the degree of suspicion of disease. In the qualitative determination result 62, it is judged that there is no suspicion of disease (negative) or there is suspicion of disease (positive) with (−) or (+), with the cut-off value of (−/+) as a boundary. In determining the degree of suspicion of disease, multiple cut-off values 55 may be included. When the cut-off value of (+/++) and the cut-off value of (++/+++) are set, (+) indicates positive, (++) indicates strong positive, and (+++) indicates stronger strong positive. Among positives, the greater the number of "+", the stronger the suspicion. As a result, by using the qualitative determination result 62 based on the measured value 51 before operation, it is possible to determine the presence or absence of suspected disease and the degree of disease without changing the qualitative determination before and after operation.

In the examples of FIGS. 26 and 27, the qualitative determination result 62 indicates the degree of suspicion for the presence or absence of cancer metastasis. That is, as described above, qualitative determination on the presence or absence of metastasis of various cancers such as breast cancer, stomach cancer and colorectal cancer may be performed. The qualitative determination result 62 indicates that there is suspicion of metastasis on the measured specimen when it is positive, and that there is no suspicion of metastasis when it is negative. Since judgment on the presence or absence of metastasis in cancer treatment is highly important, according to the above configuration, it is particularly useful in that it is possible to display a consistent determination result that does not change before and after operation, by using the qualitative determination result 62 before operation, in the qualitative determination on clinical judgment of high importance like the presence or absence of cancer metastasis.

In the examples of FIGS. 26 and 27, the measured value 51 is a measured value of at least one of the amount of a nucleic acid as the test substance 90 and the expression level of the nucleic acid. Thereby, for example, in the genetic testing, the arithmetic value 61 of the measured value 51 can be displayed together with the qualitative determination result 62 based on the measured value 51 before operation for a specific examination item. In the fields where accumulation of academic knowledge is required, like genetic testing, it is desirable to enable comparison of measured values using different measurement reagents, so that the method for displaying a qualitative determination result and the measuring apparatus 400 shown in FIGS. 26 and 27 are useful when displaying the measurement result using a nucleic acid as the test substance 90.

In the examples of FIGS. 26 and 27, the measurement using the measurement reagent 50 includes a step of amplifying a nucleic acid using the measurement reagent 50. That is, the measurement unit 410 may include the reaction section 130 shown in FIGS. 8 and 10. The reaction section 130 amplifies a nucleic acid as the test substance 90. By operating the measured value 51 of the nucleic acid amplified using the measurement reagent 50 to obtain the arithmetic value 61, it becomes possible to compare with the measured value of the nucleic acid amplified using another measurement reagent used under the second measurement condition.

In the case of including a step of amplifying a nucleic acid, amplification by the LAMP method is performed in the step of amplifying a nucleic acid. This makes it possible to quickly perform the processing of amplifying the nucleic acid using the measurement reagent 50, measuring at least one of the amount of the nucleic acid and the expression level of the nucleic acid, and acquiring the measured value 51. As a result, the time taken from the start of the measurement on the examination item until the arithmetic value 61 of the measured value 51 is obtained and can be compared with the measurement result using the other measurement reagent is shortened, and prompt clinical examination becomes possible.

In the examples of FIGS. 26 and 27, in the measurement using the measurement reagent 50 that performs amplification by the LAMP method, the measured value 51 corresponding to the amount of the test substance 90 in the sample is acquired, based on the turbidity change of the sample due to the amplification of the nucleic acid using the measurement reagent 50. That is, the measurement unit 410 may include the turbidity detection section 140 shown in FIGS. 8 and 10. This makes it possible to easily acquire the measured value 51 based on turbidity change.

In the examples of FIGS. 26 and 27, the test substance 90 is a nucleic acid whose expression level increases or decreases in cancer cells as compared with in normal cells. This makes it possible to acquire the measured value 51 and the arithmetic value 61 for performing clinical judgment such as the presence or absence of cancer metastasis, using the nucleic acid that is the test substance 90 as a marker gene.

More specifically, the test substance 90 is mRNA of cytokeratin 19. With this configuration, by using mRNA of CK19 suitable as a marker as the test substance 90 since the expression level is high in the metastasis-positive lymph node and the expression level is low in the metastasis-negative lymph node, and the individual difference is small in the expression level, clinical judgment on the presence or absence of cancer metastasis and the like can be performed with high accuracy.

In the measuring apparatus 400 shown in FIG. 27, among the measurements using the measurement reagent 50 by the measurement unit 410, for example, processing for acquiring the measured value 51 based on turbidity change, processing of qualitative determination by the determination unit 420, processing for obtaining the arithmetic value 61 by the operational unit 430, and processing for displaying the arithmetic value 61 and the qualitative determination result 62 on the display unit 440 can be performed by making a computer execute a program 500 for displaying the qualitative determination result based on the measurement result of the test substance 90. These processing may be realized by respective dedicated hardware.

In the example of FIG. 27, the program 500 makes the computer comprising the CPU 450 and the storage unit 460 acquire the measured value 51 of the test substance 90 measured under the first measurement condition, the program 500 makes the computer perform qualitative determination on a specimen containing the test substance 90 by comparing the measured value 51 with the cut-off value 55, the program 500 makes the computer obtain the arithmetic value 61 operated so as to correspond to a measured value when the measured value 51 is measured under a second measurement condition, and the program 500 makes the computer display the arithmetic value 61 and the qualitative determination result 62 on the display unit 440. By executing the program 500, the CPU 450 functions as a part of the measurement unit 410 that executes arithmetic processing for acquiring the measured value 51, the CPU 450 functions as the determination unit 420 that performs qualitative determination, the CPU 450 functions as the operational unit 430 that obtains the arithmetic value 61, and the CPU 450 functions as a control unit that controls the display unit 440 so as to display the arithmetic value 61 and the qualitative determination result 62.

In the program 500 according to the example of FIG. 27, according to the above configuration, even when displaying the arithmetic value 61 obtained by operating the measured value 51, it is possible to make a determination using the measured value 51 before operation for qualitative determination, and to display the qualitative determination result based on the measured value 51 before operation, and the arithmetic value 61. That is, even when displaying the arithmetic value 61 corresponding to the measured value in the case of using another second measurement condition different from the first measurement condition used for acquiring the measured value 51, the qualitative determination results using the measured value 51 before operation actually measured and the cut-off value 55 of the first measurement condition used for the measurement are consistently displayed, instead of performing qualitative determination using the obtained arithmetic value 61 and the cut-off value of another second measurement condition, so that consistent qualitative determination results can be displayed before and after operation. As a result, it is possible to suppress change in clinical judgment before and after operation, when operating the measured value 51 obtained using a certain first measurement condition to the value in the case of using another second measurement condition in clinical examination.

It should be considered that the embodiments disclosed herein are an example in all respects and is not restrictive. The scope of the present invention is indicated not by the description of the above embodiment but by the scope of claims, and further includes meanings equivalent to the scope of claims and all modifications (variations) within the scope.

What is claimed is:

1. A measurement method for measuring a test substance contained in a biological sample based on a predetermined measurement principle, the method comprising:
   measuring the test substance using a first measurement reagent and acquiring a first measured value;
   establishing a numerical correspondence to associate a first cut-off value for the first measured value and a second cut-off value for a second measured value, wherein the first cut-off value and the second cut-off value are thresholds for performing qualitative determination on at least one of the biological sample and a specimen containing the biological sample, wherein the second measured value is acquired by measuring the test substance using a second measurement reagent different from the first measurement reagent, wherein the first measurement reagent and the second measurement reagent are used for measuring the same test substance, wherein the first measured value and the second measured value are different measured values, and wherein the first cut-off value and the second cutoff value are different cutoff values;
   correlating the first measured value and the second measured value using the numerical correspondence between the first cut-off value and the second cut-off value to establish equivalency of the first measured value and the second measured value;
   generating a qualitatively determination test result for the test substance based on correlation of the first measured value and the second measured value according to the established equivalency of the first measured value and the second measured value; and
   displaying the qualitatively determination test result as a test result for the biological sample.

2. The measurement method according to claim 1, wherein correlation of the first measured value obtained using the first measurement reagent and the second measured value obtained using the second measurement reagent comprises correlating the first measured value that matches the first cut-off value to the second cut-off value.

3. The measurement method according to claim 2, wherein, when there are a plurality of sets of the first cut-off value and the second cut-off value corresponding to the first cut-off value, correlating the first measured value and the second measured value for each respective set of the first cut-off value and the second cut-off value corresponding to the first cut-off value.

4. The measurement method according to claim 3, wherein, when the first cut-off values are $y_1, \ldots, y_n$ (n is an integer of 2 or more), and the second cut-off values corresponding to the first cut-off values $y_1, \ldots, y_n$ are $x_1, \ldots, x_n$, respectively, correlation of the first measured value and the second measure value in each section in which the first measured value Y is $y_{n-1}$ or more and $y_n$ or less is represented by:

$$Y' = (Y - b_n)/a_n \quad (1)$$

wherein Y' is the arithmetic value, Y is the first measured value, $a_n = (y_n - y_{n-1})/(x_n - x_{n-1})$, and $b_n = y_{n-1} - (x_{n-1} \times a_n)$.

5. The measurement method according to claim 2, wherein the first cut-off value is $y_1$ and the second cut-off value is $x_1$, and the correspondence between the first cut-off value and the second cut-off value is represented by:

$$Y' = (Y - y_1)/a + x_1 \quad (2)$$

wherein Y' is the arithmetic value, Y is the first measured value, and a is a slope of the approximate straight line of a plurality of the first measured values obtained using the first measurement reagent using a plurality of biological samples, and a plurality of the second measured values obtained using the second measurement reagent using the same sample as the plurality of biological samples.

6. The measurement method according to claim 1, wherein the qualitative determination test result indicates a presence or absence of suspected disease or a degree of suspicion of disease.

7. The measurement method according to claim 6, wherein the qualitative determination test result is to determine a degree of suspicion for a presence or absence of cancer metastasis.

8. The measurement method according to claim 6, wherein the qualitative determination test result of the test substance is based on the first cut-off value, the first measured value, and the second cut-off value.

9. The measurement method according to claim 1, wherein the measurement method is a method of measuring at least one of an amount of a nucleic acid as the test substance or an expression level of the nucleic acid.

10. The measurement method according to claim 9, comprising a step of amplifying the nucleic acid using the first measurement reagent.

11. The measurement method according to claim 9, wherein the test substance is the nucleic acid whose expression level increases or decreases in cancer cells as compared with in normal cells.

12. The measurement method according to claim 1, wherein the first measurement reagent and the second measurement reagent are reagents that act on a same measurement principle and have compositions different from each other.

13. A measuring apparatus for measuring a test substance contained in a biological sample based on a predetermined measurement principle, comprising: a sample measurement circuitry configured to acquire a first measured value corresponding to the test substance using a first measurement reagent, and a controller circuitry configured to correlate the first measured value to a second measured value to generate and display a qualitatively determination test result for the test substance, the sample measurement circuitry configured to acquire the second measure value by measurement of the test substance using a second measurement reagent different from the first measurement reagent, wherein the controller circuitry is configured to establish equivalency of the first measured value and the second measured value by correlation of the first measured value to the second measured value based on a numerical correspondence of a first cut-off value for the first measured value obtained using the first measurement reagent to a second cut-off value for the second measured value obtained using the second measurement reagent, wherein the first measured value and the second measured value are different measured values, and wherein the first cut-off value and the second cutoff value are different cutoff values.

14. The measuring apparatus according to claim 13, further comprising a display unit operable to display the qualitatively determination test result generated by the controller circuitry and the first measured value acquired by the sample measurement circuitry.

15. A measuring apparatus comprising a sample measurement circuitry configured to acquire a first measured value of a test substance under a first measurement condition, a controller circuitry configured to perform a qualitative determination on a specimen containing the test substance by comparing the first measured value with a cut-off value, the controller circuitry configured to obtain correspondence between the first measured value and a second measured value measured under a second measurement condition to establish equivalency of a measurement result of the first measured value and the second measured value, and the controller circuitry configured to generate a qualitative determination test result based on the correspondence of the first measured value and the second measured value and the equivalency of the measurement result, and a display unit for displaying the correspondence between the first measured value and the second measured value, and the qualitative determination test result.

16. The measuring apparatus according to claim 15, wherein the test substance is a nucleic acid, and the sample measurement circuitry includes a reaction section for amplifying a nucleic acid using a measurement reagent.

17. A method for measuring a test substance contained in a biological sample based on a predetermined measurement principle, comprising: acquiring a first cut-off value for a first measured value of the test substance obtained using a first measurement reagent, acquiring a second cut-off value for a second measured value of the test substance obtained using a second measurement reagent, and establishing a numerical correspondence of the first cut-off value with the second cut-off value, based on the first cut-off value and the second cut-off value, correlating the first measured value obtained using the first measurement reagent and the second measured value obtained using the second measurement reagent to determine an equivalency of a measurement result of the first measured value and the second measured value based on the numerical correspondence of the first cutoff value and the second cutoff value, and generating a qualitative determination test result for the test substance based on correlation of the first measured value and the second measured value.

18. The method according to claim 17, comprising setting a first coordinate axis representing the first measured value obtained using the first measurement reagent and a second coordinate axis representing the second measured value obtained using the second measurement reagent, and establishing the correspondence of the first cut-off value with the second cut-off value as a function of a straight line passing through a point (x, y) determined by the first cut-off value on the first coordinate axis and the second cut-off value on the second coordinate axis.

19. A method for displaying a qualitative determination result, comprising: acquiring a first measured value of a test substance under a first measurement condition, performing qualitative determination on a specimen containing the test substance by comparing the first measured value with a cut-off value, obtaining correspondence of the first measured value to a second measured value based on an equivalency of the first measured value and the second measured value established according to the first measured value and the cutoff value, the second measured value measured under a second measurement condition, wherein the second measurement condition is different from the first measurement condition; and displaying a qualitative determination test result according to the correspondence of the first measured value to the second measured value.

20. A measurement method for measuring a test substance contained in a biological sample based on a predetermined measurement principle, the method comprising:

acquiring a first measured value of the test substance under a first measurement condition;

corresponding a first cut-off value for the first measurement condition to a second cut-off value for a second measured value, wherein the first cut-off value and the second cut-off value are thresholds for performing qualitative determination on at least one of the biological sample and a specimen containing the biological sample, and wherein the second measured value is acquired by measuring the test substance under a second measurement condition different from the first measurement condition;

correlating the first measured value to the second measured value to establish an equivalency of the first measured value and the second measured value according to the correspondence between the first cut-off value and the second cut-off value; and generating and displaying a qualitative determination test result based on the correlated first and second measure values.

21. A measuring apparatus for measuring a test substance contained in a biological sample based on a predetermined measurement principle, comprising:

a sample measurement circuitry configured to acquire a first measured value of the test substance under a first measurement condition;

controller circuitry configured to correspond a first cut-off value for the first measurement condition to a second cut-off value for a second measured value, wherein the first cut-off value and the second cut-off value are thresholds for performing qualitative determination on at least one of the biological sample and a specimen containing the biological sample, and wherein the second measured value is acquired by measurement, by the sample measurement circuitry, of the test substance under a second measurement condition different from the first measurement condition;

the controller circuitry further configured to correlate the first measured value to the second measured value to establish an equivalency of the first measured value and the second measured value according to the correspondence between the first cut-off value and the second cut-off value; and controller circuitry configured to generate and display in a display a qualitative determination test result based on the correlated first and second measure values.

* * * * *